US012765909B2

(12) United States Patent
Otto et al.

(10) Patent No.: US 12,765,909 B2
(45) Date of Patent: Oct. 20, 2026

(54) ROBOTIC SURGICAL SYSTEM WITH DYNAMIC RESECTION COMBINATION

(71) Applicant: MAKO Surgical Corp., Weston, FL (US)

(72) Inventors: Jason Otto, Sioux Falls, SD (US); Jill Sarah Wolfson Jacobson, Weston, FL (US); Matt Harrow, Mooresville, NC (US); Scott Logan, Mahwah, NJ (US)

(73) Assignee: MAKO SURGICAL CORP., Weston, FL (US)

( * ) Notice: Subject to any disclaimer, the term of this patent is extended or adjusted under 35 U.S.C. 154(b) by 63 days.

(21) Appl. No.: 19/028,202

(22) Filed: Jan. 17, 2025

(65) Prior Publication Data

US 2025/0261961 A1 Aug. 21, 2025

Related U.S. Application Data

(60) Provisional application No. 63/555,152, filed on Feb. 19, 2024.

(51) Int. Cl.

| | |
|---|---|
| ***A61B 34/30*** | (2016.01) |
| ***A61B 17/32*** | (2006.01) |
| ***A61B 34/00*** | (2016.01) |
| ***A61B 34/10*** | (2016.01) |

(52) U.S. Cl.

CPC .............. *A61B 17/32* (2013.01); *A61B 34/10* (2016.02); *A61B 34/25* (2016.02); *A61B 34/30* (2016.02)

(58) Field of Classification Search

CPC .......... A61B 34/10; A61B 34/30; A61B 34/32
See application file for complete search history.

(56) References Cited

U.S. PATENT DOCUMENTS

| | | | |
|---|---|---|---|
| 8,010,180 | B2 | 8/2011 | Quaid et al. |
| 9,292,567 | B2 | 3/2016 | Dua |
| 9,888,967 | B2 | 2/2018 | Granchi et al. |
| 9,913,692 | B2 | 3/2018 | Arata et al. |
| 10,595,880 | B2 | 3/2020 | Otto et al. |

(Continued)

FOREIGN PATENT DOCUMENTS

| | | | |
|---|---|---|---|
| EP | 4 070 752 | A1 | 10/2022 |

OTHER PUBLICATIONS

Invitation to pay additional fees for International Application No. PCT/US2025/013495, mailed May 19, 2025, 17 pages.

(Continued)

*Primary Examiner* — Samuel S Hanna
(74) *Attorney, Agent, or Firm* — Foley & Lardner LLP

(57) ABSTRACT

A robotically-assisted surgical system includes a robot and a computer. The computer is programmed to provide a user with an option to combine a first cutting stage of a surgical plan with a second cutting stage of the surgical plan in response to determining that the first cutting stage is eligible for combination with the second cutting stage by comparing first characteristics of the first cutting stage with second characteristics of the second cutting stage. The computer is also programmed to, absent selection of the option, control the robot to provide the first cutting stage and the second cutting stage sequentially and also to, in response to user selection of the option, control the robot to provide a unified cutting stage based on the first cutting stage and the second cutting stage.

12 Claims, 10 Drawing Sheets

(56) References Cited

U.S. PATENT DOCUMENTS

| | | | |
|---|---|---|---|
| 11,478,362 B2 | 10/2022 | Thompson et al. | |
| 11,523,867 B2 | 12/2022 | Greenwald et al. | |
| 11,684,374 B2 | 6/2023 | Kang et al. | |
| 11,864,836 B2 | 1/2024 | Ikits et al. | |
| 11,937,831 B2 | 3/2024 | Nadzadi et al. | |
| 2009/0234217 A1 | 9/2009 | Mire et al. | |
| 2019/0117311 A1 | 4/2019 | Bellettre et al. | |
| 2022/0071720 A1 | 3/2022 | Sexson et al. | |
| 2024/0173096 A1 * | 5/2024 | Forstein ................. | A61B 34/10 |

OTHER PUBLICATIONS

International Search Report and Written Opinion for International Application No. PCT/US2025/013495, mailed Jul. 11, 2025, 21 pages.

* cited by examiner

ROBOTIC SURGICAL SYSTEM WITH DYNAMIC RESECTION COMBINATION

CROSS-REFERENCE TO RELATED APPLICATION

This application claims the benefit of and priority to U.S. Provisional Application No. 63/555,152 filed Feb. 19, 2024, the entire disclosure of which is incorporated by reference herein.

BACKGROUND

The present disclosure relates generally to surgical systems for orthopedic surgeries, for example surgical systems that facilitate joint replacement procedures. Joint replacement procedures (arthroplasty procedures) are widely used to treat osteoarthritis and other damage to a patient's joint by replacing portions of the joint with prosthetic components. Joint replacement procedures can include procedures to replace hips, knees, shoulders, or other joints with one or more prosthetic components.

One possible tool for use in an arthroplasty procedure is a robotically-assisted surgical system. A robotically-assisted surgical system typically includes a robotic device that is used to prepare a patient's anatomy to receive an implant, a tracking system configured to monitor the location of the robotic device relative to the patient's anatomy, and a computing system configured to monitor and control the robotic device. Robotically-assisted surgical systems, in various forms, autonomously carry out surgical tasks, provide force feedback to a user manipulating a surgical device to complete surgical tasks, augment surgeon dexterity and precision, and/or provide other navigational cues to facilitate safe and accurate surgical operations.

A surgical plan is typically established prior to performing a surgical procedure with a robotically-assisted surgical system. Based on the surgical plan, the surgical system guides, controls, or limits movements of the surgical device during portions of the surgical procedure. Guidance and/or control of the surgical device serves to assist the surgeon during implementation of the surgical plan. The surgical plan can include multiple stages, for example to be executed on different bones and/or to prepare different surfaces, shapes, recesses, holes, etc. on a given bone, which may typically be executed sequentially. Various features enhancing surgical robot control in scenarios involving multiple surgical stages would be advantageous.

SUMMARY

Figure 1:
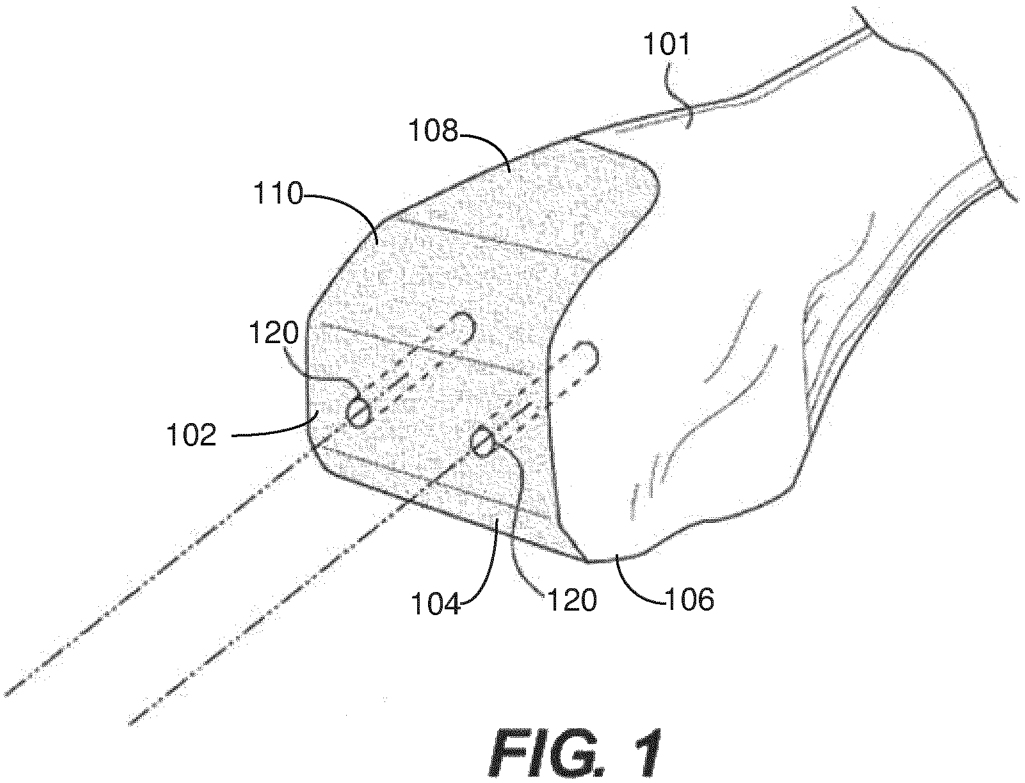
FIG. 1 is a perspective view of a femur prepared to receive an implant component, according to an exemplary embodiment.

One implementation of the present disclosure is a robotically-assisted surgical system. The robotically-assisted surgical system includes a robot and computer. The computer is programmed to provide a user with an option to combine a first cutting stage of a surgical plan with a second cutting stage of the surgical plan in response to determining that the first cutting stage is eligible for combination with the second cutting stage by comparing first characteristics of the first cutting stage with second characteristics of the second cutting stage, and abstain from providing the user with the option to combine the first cutting stage with the second cutting stage in response to determining that the first cutting stage is ineligible for combination with the second cutting stage by comparing the first characteristics with the second characteristics. The computer is also programmed to control the robot to provide, absent selection of the option, the first cutting stage and the second cutting stage sequentially. The computer is also programmed to control the robot to provide, in response to user selection of the option, a unified cutting stage based on the first cutting stage and the second cutting stage.

Another implementation of the present disclosure is at least one non-transitory computer-readable medium storing program instructions that, when executed by one or more processors, cause the one or more processors to perform operations (e.g., such instructions can be stored one or more media, memory devices, etc., for execution to perform the operations described herein). The operations include generating an option to combine a first cutting stage of a surgical plan with a second cutting stage of the surgical plan in response to determining that the first cutting stage is eligible for combination with the second cutting stage by comparing first characteristics of the first cutting stage with second characteristics of the second cutting stage. The operations also include causing a robot to operate in accordance with selection or rejection of the option by generating, in response to the rejection of the option, a first control boundary or path for the first cutting stage and a second control boundary or path for the second cutting stage, the first control boundary or path distinct from the second control boundary or path and generating, in response to the selection of the option, a unified control boundary or path for unified execution of the first cutting stage and the second cutting stage.

Another implementation of the present disclosure is a method for robotically-assisted surgery. The method includes generating an option to combine a first cutting stage of a surgical plan with a second cutting stage of the surgical plan in response to determining that the first cutting stage is eligible for combination with the second cutting stage by comparing first characteristics of the first cutting stage with second characteristics of the second cutting stage. The method also includes causing a robot to operate in accordance with selection or rejection of the option by generating, in response to the rejection of the option, a first control boundary or path for the first cutting stage and a second control boundary or path for the second cutting stage, the first control boundary or path distinct from the second control boundary or path and generating, in response to the selection of the option, a unified control boundary or path for unified execution of the first cutting stage and the second cutting stage.

DETAILED DESCRIPTION

Presently preferred embodiments of the invention are illustrated in the drawings. An effort has been made to use the same or like reference numbers throughout the drawings to refer to the same or like parts. Although this specification refers primarily to a robotic arm for orthopedic joint replacement, it should be understood that the subject matter described herein is applicable to other types of robotic systems, including those used for non-surgical applications, as well as for procedures directed to other anatomical regions, for example spinal or dental procedures.

Surgical Robotics System

Referring now to FIG. 1, a femur 101 as modified during a knee arthroplasty procedure is shown, according to an exemplary embodiment. As shown in FIG. 1, the femur 101 has been modified with multiple planar cuts. In the example shown, the femur 101 has been modified by five substantially planar cuts to create five substantially planar surfaces, namely distal surface 102, posterior chamfer surface 104, posterior surface 106, anterior surface 108, and anterior chamfer surface 110. The planar surfaces may be achieved using a sagittal saw or other surgical device, for example a surgical device coupled to a robotic device as in the examples described below. The planar surfaces 102-110 are created such that the planar surfaces 102-110 will mate with corresponding surfaces of a femoral implant component. The positions and angular orientations of the planar surfaces 102-110 may determine the alignment and positioning of the implant component. Accordingly, operating a surgical device to create the planar surfaces 102-110 with a high degree of accuracy may improve the outcome of a joint replacement procedure.

As shown in FIG. 1, the femur 101 has also been modified to have a pair of pilot holes 120. The pilot holes 120 extend into the femur 101 and are created such that the pilot holes 120 can receive a screw, a projection extending from a surface of an implant component, or other structure configured to facilitate coupling of an implant component to the femur 101. The pilot holes 120 may be created using a drill, spherical burr, or other surgical device as described herein. The pilot holes 120 may have a pre-planned position, orientation, and depth, which facilitates secure coupling of the implant component to the bone in a desired position and orientation. In some cases, the pilot holes 120 are planned to intersect with higher-density areas of a bone and/or to avoid other implant components and/or sensitive anatomical features. Accordingly, operating a surgical device to create the pilot holes 120 with a high degree of accuracy may improve the outcome of a joint replacement procedure.

A tibia may also be modified during a joint replacement procedure. For example, a planar surface may be created on the tibia at the knee joint to prepare the tibia to mate with a tibial implant component. In some embodiments, one or more pilot holes 120 or other recess (e.g., fin-shaped recess) may also be created in the tibia to facilitate secure coupling of an implant component tot eh bone.

In some embodiments, the systems and methods described herein provide robotic assistance for creating the planar surfaces 102-110 and the pilot holes 120 at the femur 101, and/or a planar surface and/or pilot holes 120 or other recess on a tibia. It should be understood that the creation of five planar cuts and two cylindrical pilot holes as shown in FIG. 1 is an example only, and that the systems and methods described herein may be adapted to plan and facilitate creation of any number of planar or non-planar cuts, any number of pilot holes, any combination thereof, etc., for preparation of any bone and/or joint in various embodiments. For example, in a hip or shoulder arthroplasty procedure, a spherical burr may be used in accordance with the systems and methods herein to ream a curved surface configured to receive a curved implant cup. Furthermore, in other embodiments, the systems and methods described herein may be used to facilitate placement an implant component relative to a bone (e.g., to facilitate impaction of cup implant in a hip arthroplasty procedure). Many such surgical and non-surgical implementations are within the scope of the present disclosure.

The positions and orientations of the planar surfaces 102-110, pilot holes 120, and any other surfaces or recesses created on bones of the knee joint can affect how well implant components mate to the bone as well as the resulting biomechanics for the patient after completion of the surgery. Tension on soft tissue can also be affected. Accordingly, systems and methods for planning the cuts which create these surfaces, facilitating intra-operative adjustments to the surgical plan, and providing robotic-assistance or other guidance for facilitating accurate creation of the planar surfaces 102-110, other surfaces, pilot holes 120, or other recesses can make surgical procedures easier and more efficient for healthcare providers and improve surgical outcomes.

Figure 2:
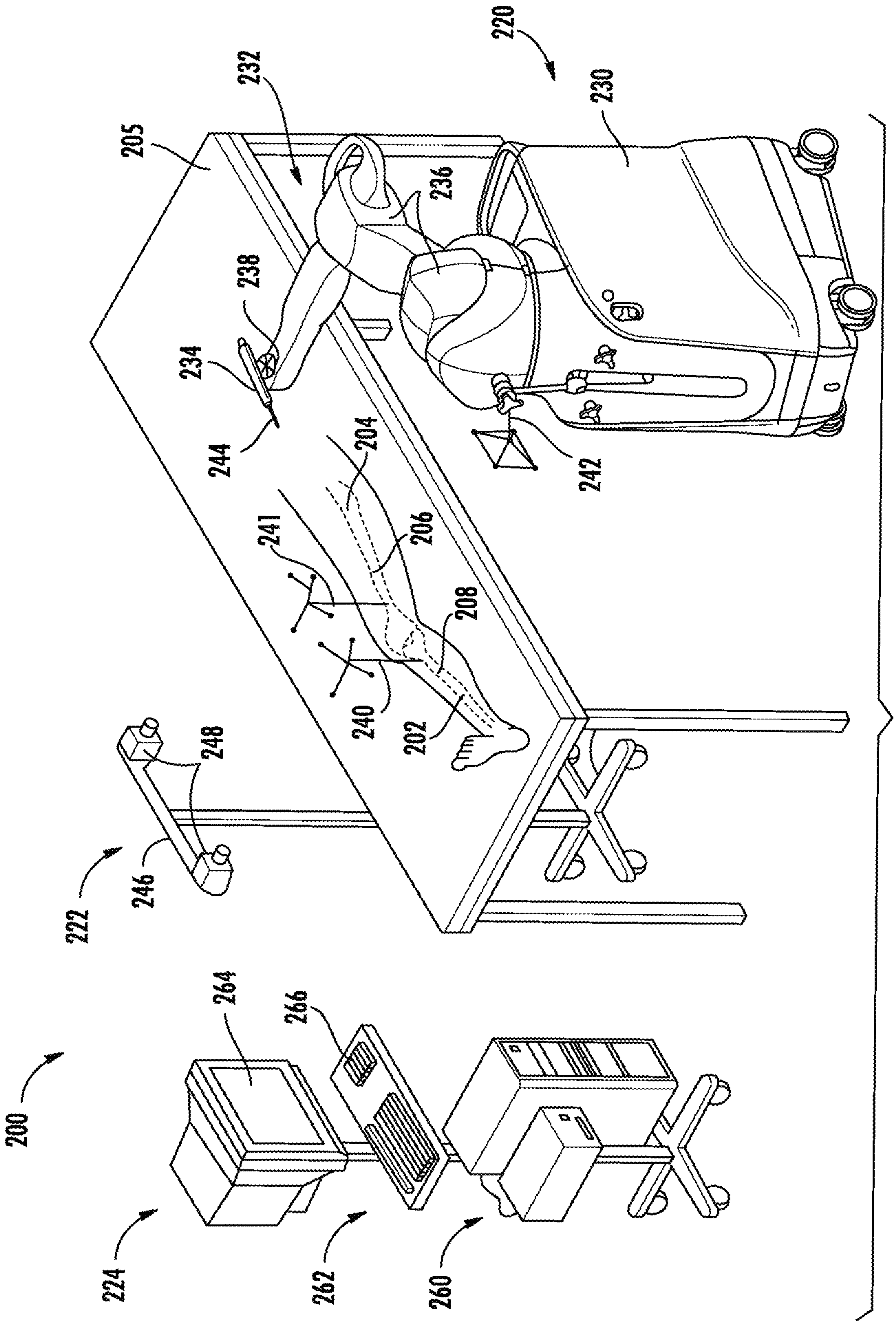
FIG. 2 is an illustration of a surgical system, according to an exemplary embodiment.

Referring now to FIG. 2, a surgical system 200 for orthopedic surgery is shown, according to an exemplary embodiment. In general, the surgical system 200 is configured to facilitate the planning and execution of a surgical plan, for example to facilitate a joint-related procedure. As shown in FIG. 2, the surgical system 200 is set up to treat a leg 202 of a patient 204 sitting or lying on table 205. In the illustration shown in FIG. 2, the leg 202 includes femur 206 (e.g., femur 101 of FIG. 1) and tibia 208, between which a prosthetic knee implant is to be implanted in a total knee arthroscopy procedure. In other scenarios, the surgical system 200 is set up to treat a hip of a patient, e.g., the femur and the pelvis of the patient. Additionally, in still other scenarios, the surgical system 200 is set up to treat a shoulder of a patient, e.g., to facilitate replacement and/or augmentation of components of a shoulder joint (e.g., to facilitate placement of a humeral component, a glenoid component, and a graft or implant augment). Various other anatomical regions and procedures are also possible.

The robotic device 220 is configured to modify a patient's anatomy (e.g., femur 206 of patient 204) under the control of the computing system 224. One embodiment of the robotic device 220 is a haptic device. "Haptic" refers to a sense of touch, and the field of haptics relates to, among other things, human interactive devices that provide feedback to an operator. Feedback may include tactile sensations such as, for example, vibration. Feedback may also include providing force to a user, such as a positive force or a resistance to movement. One use of haptics is to provide a user of the device with guidance or limits for manipulation of that device. For example, a haptic device may be coupled to a surgical device, which can be manipulated by a surgeon to perform a surgical procedure. The surgeon's manipulation of the surgical device can be guided or limited through the use of haptics to provide feedback to the surgeon during manipulation of the surgical device.

Another embodiment of the robotic device 220 is an autonomous or semi-autonomous robot. "Autonomous" refers to a robotic device's ability to act independently or semi-independently of human control by gathering information about its situation, determining a course of action, and automatically carrying out that course of action. For example, in such an embodiment, the robotic device 220, in communication with the tracking system 222 and the computing system 224, may autonomously complete the series of femoral cuts mentioned above without direct human intervention.

The robotic device 220 includes a base 230, a robotic arm 232, and a surgical device 234, and is communicably coupled to the computing system 224 and the tracking system 222. The base 230 provides a moveable foundation for the robotic arm 232, allowing the robotic arm 232 and the surgical device 234 to be repositioned as needed relative to the patient 204 and the table 205. The base 230 may also contain power systems, computing elements, motors, and other electronic or mechanical system necessary for the functions of the robotic arm 232 and the surgical device 234 described below.

The robotic arm (robot) 232 is configured to support the surgical device 234 and provide a force as instructed by the computing system 224. In some embodiments, the robotic arm 232 allows a user to manipulate the surgical device and provides force feedback to the user. In such an embodiment, the robotic arm 232 includes joints 236 and mount 238 that include motors, actuators, or other mechanisms configured to allow a user to freely translate and rotate the robotic arm 232 and surgical device 234 through allowable poses while providing force feedback to constrain or prevent some movements of the robotic arm 232 and surgical device 234 as instructed by computing system 224. As described in detail below according to various embodiments, the robotic arm 232 thereby allows a surgeon to have full control over the surgical device 234 within a control object while providing force feedback along a boundary of that object (e.g., a vibration, a force preventing or resisting penetration of the boundary). In some embodiments, the robotic arm 232 is configured to move the surgical device to a new pose automatically without direct user manipulation, as instructed by computing system 224, in order to position the robotic arm 232 as needed and/or complete certain surgical tasks, including, for example, cuts in a femur 206.

The surgical device 234 is configured to cut, burr, grind, drill, partially resect, reshape, and/or otherwise modify a bone. The surgical device 234 may be any suitable tool, and may be one of multiple tools interchangeably connectable to robotic device 220. For example, as shown in FIG. 2 the surgical device 234 includes a spherical burr 244. In other examples, the surgical device 234 may also be a sagittal saw, for example with a blade aligned parallel with a tool axis or perpendicular to the tool axis. The surgical device 234 may also be a drill, for example with a rotary bit aligned parallel with a tool axis or perpendicular to the tool axis. The surgical device 234 may also be a holding arm or other support configured to hold an implant component (e.g., cup, implant augment, etc.) in position while the implant component is screwed to a bone, adhered (e.g., cemented) to a bone or other implant component, or otherwise installed in a preferred position. In some embodiments, the surgical device 234 is an impaction tool configured to provide an impaction force to a cup implant to facilitate fixation of the cup implant to a pelvis in a planned location and orientation.

Tracking system 222 is configured track the patient's anatomy (e.g., femur 206 and tibia 208) and the robotic device 220 (e.g., surgical device 234 and/or robotic arm 232) to enable control of the surgical device 234 coupled to the robotic arm 232, to determine a position and orientation of modifications or other results made by the surgical device 234, and allow a user to visualize the bones (e.g., femur 206, the tibia 208, pelvis, humerus, scapula, etc. as applicable in various procedures), the surgical device 234, and/or the robotic arm 232 on a display of the computing system 224. The tracking system 222 can also be used to collect biomechanical measurements relating to the patient's anatomy, assess joint gap distances, identify a hip center point, assess native or corrected joint deformities, or otherwise collect information relating to the relative poses of anatomical features. More particularly, the tracking system 222 determines a position and orientation (e.g., pose) of objects (e.g., surgical device 234, femur 206) with respect to a coordinate frame of reference and tracks (e.g., continuously determines) the pose of the objects during a surgical procedure. According to various embodiments, the tracking system 222 may be any type of navigation system, including a non-mechanical tracking system (e.g., an optical tracking system), a mechanical tracking system (e.g., tracking based on measuring the relative angles of joints 236 of the robotic arm 232), or any combination of non-mechanical and mechanical tracking systems.

In the embodiment shown in FIG. 2, the tracking system 222 includes an optical tracking system. Accordingly, tracking system 222 includes a first fiducial tree 240 coupled to the tibia 208, a second fiducial tree 241 coupled to the femur 206, a third fiducial tree 242 coupled to the base 230, one or more fiducials attachable to surgical device 234, and a detection device 246 configured to detect the three-dimensional position of fiducials (e.g., markers on fiducial trees 240-242). Fiducial trees 240, 241 may be coupled to other bones as suitable for various procedures (e.g., pelvis and femur in a hip arthroplasty procedure). Detection device 246 may be an optical detector such as a camera or infrared sensor. The fiducial trees 240-242 include fiducials, which are markers configured to show up clearly to the optical detector and/or be easily detectable by an image processing system using data from the optical detector, for example by being highly reflective of infrared radiation (e.g., emitted by an element of tracking system 222). In some embodiments, the markers are active light emitting diodes. A stereoscopic arrangement of cameras 248 on detection device 246 allows the position of each fiducial to be determined in 3D-space through a triangulation approach in the example shown. Each fiducial has a geometric relationship to a corresponding object, such that tracking of the fiducials allows for the tracking of the object (e.g., tracking the second fiducial tree 241 allows the tracking system 222 to track the femur 206), and the tracking system 222 may be configured to carry out a registration process to determine or verify this geometric relationship. Unique arrangements of the fiducials in the fiducial trees 240-242 (e.g., the fiducials in the first fiducial tree 240 are arranged in a different geometry than fiducials in the second fiducial tree 241) allows for distinguishing the fiducial trees, and therefore the objects being tracked, from one another.

Using the tracking system 222 of FIG. 2 or some other approach to surgical navigation and tracking, the surgical system 200 can determine the position of the surgical device 234 relative to a patient's anatomical feature, for example femur 206, as the surgical device 234 is used to modify the anatomical feature or otherwise facilitate the surgical procedure. Additionally, using the tracking system 222 of FIG. 2 or some other approach to surgical navigation and tracking, the surgical system 200 can determine the relative poses of the tracked bones.

The computing system 224 is configured to create a surgical plan, control the robotic device 220 in accordance with the surgical plan to make one or more bone modifications and/or facilitate implantation of one or more prosthetic components. Accordingly, the computing system 224 is communicably coupled to the tracking system 222 and the robotic device 220 to facilitate electronic communication between the robotic device 220, the tracking system 222, and the computing system 224. Further, the computing system 224 may be connected to a network to receive information related to a patient's medical history or other patient profile information, medical imaging, surgical plans, surgical procedures, and to perform various functions related to performance of surgical procedures, for example by accessing an electronic health records system. Computing system 224 includes processing circuit 260 and input/output device 262. Computing system 224 may include circuitry configured to enable the operations described herein, for example using processing circuit 260 and/or input/output device 262.

The input/output device 262 is configured to receive user input and display output as needed for the functions and processes described herein. As shown in FIG. 2, input/output device 262 includes a display 264 and a keyboard 266. The display 264 is configured to display graphical user interfaces generated by the processing circuit 260 that include, for example, information about surgical plans, medical imaging, settings and other options for surgical system 200, status information relating to the tracking system 222 and the robotic device 220, and tracking visualizations based on data supplied by tracking system 222. The keyboard 266 is configured to receive user input to those graphical user interfaces to control one or more functions of the surgical system 200.

The processing circuit 260 includes a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer-readable media for completing or facilitating the various processes and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit 260 and includes computer-readable media for executing (e.g., by the processing circuit 260 and/or processor) one or more processes described herein, for example non-transitory computer-readable media.

More particularly, processing circuit 260 is configured to facilitate the creation of a preoperative surgical plan prior to the surgical procedure. According to some embodiments, the preoperative surgical plan is developed utilizing a three-dimensional representation of a patient's anatomy, also referred to herein as a "virtual bone model." A "virtual bone model" may include virtual representations of cartilage or other tissue in addition to bone. To obtain the virtual bone model, the processing circuit 260 receives imaging data of the patient's anatomy on which the surgical procedure is to be performed. The imaging data may be created using any suitable medical imaging technique to image the relevant anatomical feature, including computed tomography (CT), magnetic resonance imaging (MRI), and/or ultrasound. The imaging data is then segmented (e.g., the regions in the imaging corresponding to different anatomical features are distinguished) to obtain the virtual bone model. For example, MRI-based scan data of a joint can be segmented to distinguish bone from surrounding ligaments, cartilage, previously-implanted prosthetic components, and other tissue to obtain a three-dimensional model of the imaged bone.

Alternatively, the virtual bone model may be obtained by selecting a three-dimensional model from a database or library of bone models. In one embodiment, the user may use input/output device 262 to select an appropriate model. In another embodiment, the processing circuit 260 may execute stored instructions to select an appropriate model based on images or other information provided about the patient. The selected bone model(s) from the database can then be deformed based on specific patient characteristics, creating a virtual bone model for use in surgical planning and implementation as described herein.

A preoperative surgical plan can then be created based on the virtual bone model. The surgical plan may be automatically generated by the processing circuit 260, input by a user via input/output device 262, or some combination of the two (e.g., the processing circuit 260 limits some features of user-created plans, generates a plan that a user can modify, etc.). In some embodiments, the surgical plan may be generated and/or modified based on distraction force measurements collected intraoperatively.

The preoperative surgical plan includes the desired cuts, holes, surfaces, burrs, or other modifications to a patient's anatomy to be made using the surgical system 200. For example, for a total knee arthroscopy procedure, the preoperative plan may include the cuts necessary to form, on a femur, a distal surface, a posterior chamfer surface, a posterior surface, an anterior surface, and an anterior chamfer surface in relative orientations and positions suitable to be mated to corresponding surfaces of the prosthetic to be joined to the femur during the surgical procedure, as well as cuts necessary to form, on the tibia, surface(s) suitable to mate to the prosthetic to be joined to the tibia during the surgical procedure. As another example, the preoperative plan may include the modifications necessary to create holes (e.g., pilot holes 120) in a bone. As another example, in a hip arthroplasty procedure, the surgical plan may include the burr necessary to form one or more surfaces on the acetabular region of the pelvis to receive a cup and, in suitable cases, an implant augment. Accordingly, the processing circuit 260 may receive, access, and/or store a model of the prosthetic to facilitate the generation of surgical plans. In some embodiments, the processing circuit facilitate intraoperative modifications to the preoperative plant.

The processing circuit 260 is further configured to generate a control object for the robotic device 220 in accordance with the surgical plan. The control object may take various forms according to the various types of possible robotic devices (e.g., haptic, autonomous). For example, in some embodiments, the control object defines instructions for the robotic device 220 to control the robotic device 220 to move within the control object (e.g., to autonomously make one or more cuts of the surgical plan guided by feedback from the tracking system 222). In some embodiments, the control object includes a visualization of the surgical plan and the robotic device 220 on the display 264 to facilitate surgical navigation and help guide a surgeon to follow the surgical plan (e.g., without active control or force feedback of the robotic device). In embodiments where the robotic device 220 is a haptic device, the control object may be a haptic object as described in the following paragraphs.

In an embodiment where the robotic device 220 is a haptic device, the processing circuit 260 is further configured to generate one or more haptic objects based on the preoperative surgical plan to assist the surgeon during implementation of the surgical plan by enabling constraint of the surgical device 234 during the surgical procedure. A haptic object may be formed in one, two, or three dimensions. For example, a haptic object can be a line, a plane, or a three-dimensional volume. A haptic object may be curved with curved surfaces and/or have flat surfaces, and can be any shape, for example a funnel shape. Haptic objects can be created to represent a variety of desired outcomes for movement of the surgical device 234 during the surgical procedure. One or more of the boundaries of a three-dimensional haptic object may represent one or more modifications, such as cuts, to be created on the surface of a bone. A planar haptic object may represent a modification, such as a cut, to be created on the surface of a bone. A curved haptic object may represent a resulting surface of a bone as modified to receive a cup implant and/or implant augment. A line haptic object may correspond to a pilot hole to be made in a bone to prepare the bone to receive a screw or other projection.

In an embodiment where the robotic device 220 is a haptic device, the processing circuit 260 is further configured to generate a virtual tool representation of the surgical device 234. The virtual tool includes one or more haptic interaction points (HIPs), which represent and are associated with locations on the surgical device 234. In an embodiment in which the surgical device 234 is a spherical burr (e.g., as shown in FIG. 2), a HIP may represent the center of the spherical burr. Where one HIP is used to virtually represent a surgical device, the HIP may be referred to herein as a tool center point (TCP). If the surgical device 234 is an irregular shape, for example as for a sagittal saw, the virtual representation of the sagittal saw may include numerous HIPs. Using multiple HIPs to generate haptic forces (e.g. positive force feedback or resistance to movement) on a surgical device is described in U.S. application Ser. No. 13/339,369, titled "System and Method for Providing Substantially Stable Haptics," filed Dec. 28, 2011, and hereby incorporated by reference herein in its entirety. In one embodiment of the present invention, a virtual tool representing a sagittal saw includes eleven HIPs. As used herein, references to an "HIP" are deemed to also include references to "one or more HIPs." As described below, relationships between HIPs and haptic objects enable the surgical system 200 to constrain the surgical device 234.

Prior to performance of the surgical procedure, the patient's anatomy (e.g., femur 206) is registered to the virtual bone model of the patient's anatomy by any known registration technique. One possible registration technique is point-based registration, as described in U.S. Pat. No. 8,010,180, titled "Haptic Guidance System and Method," granted Aug. 30, 2011, and hereby incorporated by reference herein in its entirety. Alternatively, registration may be accomplished by 2D/3D registration utilizing a hand-held radiographic imaging device, as described in U.S. application Ser. No. 13/562,163, titled "Radiographic Imaging Device," filed Jul. 30, 2012, and hereby incorporated by reference herein in its entirety. Registration also includes registration of the surgical device 234 to a virtual tool representation of the surgical device 234, so that the surgical system 200 can determine and monitor the pose of the surgical device 234 relative to the patient (e.g., to femur 206). Registration of allows for accurate navigation, control, and/or force feedback during the surgical procedure.

The processing circuit 260 is configured to monitor the virtual positions of the virtual tool representation, the virtual bone model, and the control object (e.g., virtual haptic objects) corresponding to the real-world positions of the patient's bone (e.g., femur 206), the surgical device 234, and one or more lines, planes, or three-dimensional spaces defined by forces created by robotic device 220. For example, if the patient's anatomy moves during the surgical procedure as tracked by the tracking system 222, the processing circuit 260 correspondingly moves the virtual bone model. The virtual bone model therefore corresponds to, or is associated with, the patient's actual (i.e. physical) anatomy and the position and orientation of that anatomy in real/physical space. Similarly, any haptic objects, control objects, or other planned automated robotic device motions created during surgical planning that are linked to cuts, modifications, etc. to be made to that anatomy also move in correspondence with the patient's anatomy. In some embodiments, the surgical system 200 includes a clamp or brace to substantially immobilize the femur 206 to minimize the need to track and process motion of the femur 206.

For embodiments where the robotic device 220 is a haptic device, the surgical system 200 is configured to constrain the surgical device 234 based on relationships between HIPs and haptic objects. That is, when the processing circuit 260 uses data supplied by tracking system 222 to detect that a user is manipulating the surgical device 234 to bring a HIP in virtual contact with a haptic object, the processing circuit 260 generates a control signal to the robotic arm 232 to provide haptic feedback (e.g., a force, a vibration) to the user to communicate a constraint on the movement of the surgical device 234. In general, the term "constrain," as used herein, is used to describe a tendency to restrict movement. However, the form of constraint imposed on surgical device 234 depends on the form of the relevant haptic object. A haptic object may be formed in any desirable shape or configuration. As noted above, three exemplary embodiments include a line, plane, or three-dimensional volume. In one embodiment, the surgical device 234 is constrained because a HIP of surgical device 234 is restricted to movement along a linear haptic object. In another embodiment, the haptic object is a three-dimensional volume and the surgical device 234 may be constrained by substantially preventing movement of the HIP outside of the volume enclosed by the walls of the three-dimensional haptic object. In another embodiment, the surgical device 234 is constrained because a planar haptic object substantially prevents movement of the HIP outside of the plane and outside of the boundaries of the planar haptic object. For example, the processing circuit 260 can establish a planar haptic object corresponding to a planned planar distal cut needed to create a distal surface on the femur 206 in order to confine the surgical device 234 substantially to the plane needed to carry out the planned distal cut.

For embodiments where the robotic device 220 is an autonomous device, the surgical system 200 is configured to autonomously move and operate the surgical device 234 in accordance with the control object. For example, the control object may define areas relative to the femur 206 for which a cut should be made. In such a case, one or more motors, actuators, and/or other mechanisms of the robotic arm 232 and the surgical device 234 are controllable to cause the surgical device 234 to move and operate as necessary within the control object to make a planned cut, for example using tracking data from the tracking system 222 to allow for closed-loop control.

Figure 3:
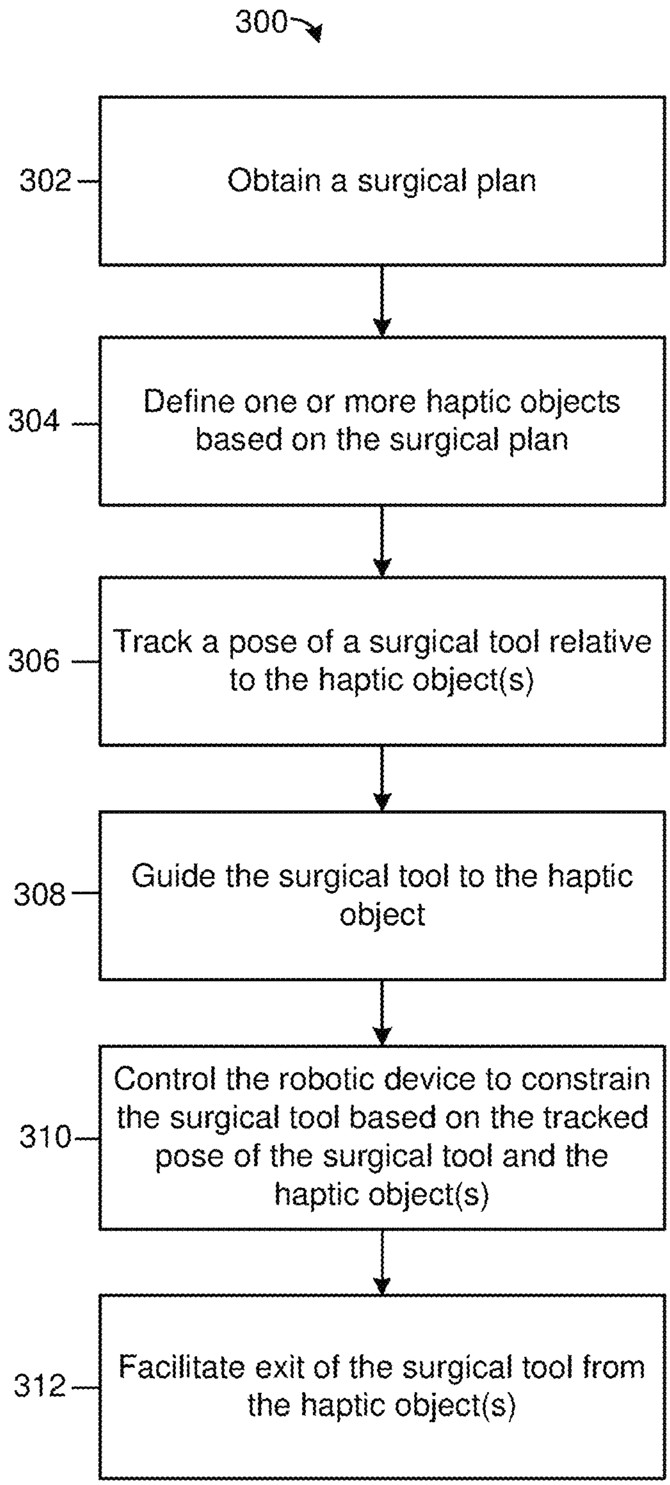
FIG. 3 is a flowchart of a first process that can be executed by the surgical system of FIG. 2, according to an exemplary embodiment.

Referring now to FIG. 3, a flowchart of a process 300 that can be executed by the surgical system 200 of FIG. 2 is shown, according to an exemplary embodiment. Process 300 may be adapted to facilitate various surgical procedures, including total and partial joint replacement surgeries.

At step 302, a surgical plan is obtained. The surgical plan (e.g., a computer-readable data file) may define a desired outcome of bone modifications, for example defined based on a desired position of prosthetic components relative to the patient's anatomy. For example, in the case of a knee arthroplasty procedure, the surgical plan may provide planned positions and orientations of the planar surfaces 102-110 and the pilot holes 120 as shown in FIG. 1. The surgical plan may be generated based on medical imaging, 3D modeling, surgeon input, etc.

At step 304, one or more control boundaries, such as haptic objects, are defined based on the surgical plan. The one or more haptic objects may be one-dimensional (e.g., a line haptic), two dimensional (e.g., planar), or three dimensional (e.g., cylindrical, funnel-shaped, curved, etc.). The haptic objects may represent planned bone modifications (e.g., a haptic object for each of the planar surfaces 102-110 and each of the pilot holes 120 shown in FIG. 1), implant components, surgical approach trajectories, etc. defined by the surgical plan. The haptic objects can be oriented and positioned in three-dimensional space relative to a tracked position of a patient's anatomy.

At step 306, a pose of a surgical device is tracked relative to the haptic object(s), for example by the tracking system 222 described above. In some embodiments, one point on the surgical device is tracked. In other embodiments, (e.g., in the example of FIGS. 4-5) two points on the surgical device are tracked, for example a tool center point (TCP) at a tip/effective end of the surgical device and a second interaction point (SIP) positioned along a body or handle portion of the surgical device. In other embodiments, three or more points on the surgical device are tracked. A pose of the surgical device is ascertained relative to a coordinate system in which the one or more haptic objects are defined and, in some embodiments, in which the pose of one or more anatomical features of the patient is also tracked.

At step 308, the surgical device is guided to the haptic object(s). For example, the display 264 of the surgical system 200 may display a graphical user interface instructing a user on how (e.g., which direction) to move the surgical device and/or robotic device to bring the surgical device to a haptic object. As another example, the surgical device may be guided to a haptic object using a collapsing haptic boundary as described in U.S. Pat. No. 9,289,264, the entire disclosure of which is incorporated by reference herein. As another example, the robotic device may be controlled to automatically move the surgical device to a haptic object.

In an embodiment where the robotic device is controlled to automatically move the surgical device to the haptic object (referred to as motorized alignment or automated alignment), the robotic device may be controlled so that a duration of the alignment is bounded by preset upper and lower time thresholds. That is, across various instances of process 300 and multiple procedures, automated alignment in step 308 may be configured to always take between a first amount of time (the lower time threshold) and a second amount of time (the upper time threshold). The lower time threshold may be selected such that the robotic device moves over a long enough duration to be perceived as well-controlled and to minimize collision or other risks associated with high speed. The upper time threshold may be selected such that the robotic device moves over a short enough duration to avoid user impatience and provide improved usability. For example, the upper time threshold hold may be approximately five seconds in an example where the lower time thresholds is approximately three seconds. In other embodiments, a single duration setpoint is used (e.g., four seconds). Step 308 can include optimizing a path for the robotic device such that the step 308 ensures successful alignment to the haptic object while also satisfying the upper and lower time thresholds or duration setpoint.

At step 310, the robotic device is controlled to constrain movement of the surgical device based on the tracked pose of the surgical device and the poses of one or more haptic objects. The constraining of the surgical device may be achieved as described above with reference to FIG. 2.

At step 312, exit of the surgical device from the haptic object(s) is facilitated, e.g., to release the constraints of a haptic object. For example, in some embodiments, the robotic device is controlled to allow the surgical device to exit a haptic object along an axis of the haptic object. In some embodiments, the surgical device may be allowed to exit the haptic object in a pre-determined direction relative to the haptic object. The surgical device may thereby be removed from the surgical field and the haptic object to facilitate subsequent steps of the surgical procedure. Additionally, it should be understood that, in some cases, the process 300 may return to step 308 where the surgical device is guided to the same or different haptic object after exiting a haptic object at step 312.

Process 300 may thereby be executed by the surgical system 200 to facilitate a surgical procedure. Features of process 300 are shown in FIGS. 4-14 below according to some embodiments, and such features can be combined in various combinations in various embodiments and/or based on settings selected for a particular procedure. Furthermore, it should be understood that the features of FIGS. 4-14 may be provided while omitting some or all other steps of process 300. All such possibilities are within the scope of the present disclosure.

Figure 4:
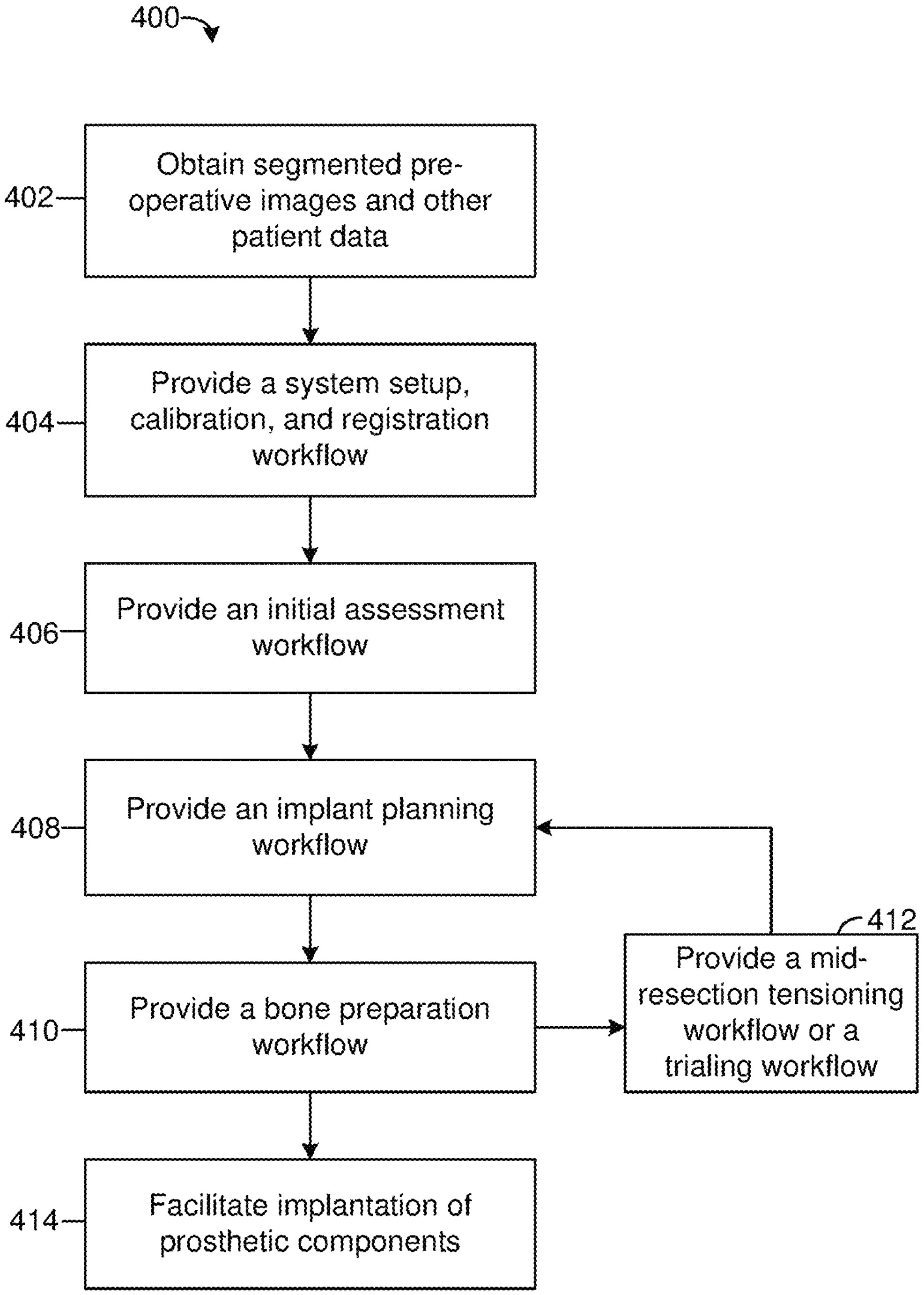
FIG. 4 is a flowchart of a second process that can be executed by the surgical system of FIG. 2, according to an exemplary embodiment.

Referring now to FIG. 4, a flowchart of a process 400 for facilitating surgical planning and guidance is shown, according to an exemplary embodiment. The process 400 may be executed by the surgical system 200 of FIG. 2, in some embodiments. In some cases, the process 300 is executed as part of executing the process 400.

At step 402, segmented pre-operative images and other patient data are obtained, for example by the surgical system 200. For example, segmented pre-operative CT images or MRI images may be received at the computing system 224 from an external server. In some cases, pre-operative images of a patient's anatomy are collected using an imaging device and segmented by a separate computing system and/or with manual user input to facilitate segmentation. In other embodiments, unsegmented pre-operative images are received at the computing system 224 and the computing system 224 is configured to automatically segment the images. The segmented pre-operative images can show the geometry, shape, size, density, and/or other characteristics of bones of a joint which is to be operated on in a procedure performed using process 400.

Other patient data can also be obtained at step 402. For example, the computing system 224 may receive patient information from an electronic medical records system. As another example, the computing system 224 may accept user input of patient information. The other patient data may include a patient's name, identification number, biographical information (e.g., age, weight, etc.), other health conditions, etc. In some embodiments, the patient data obtained at step 402 includes information specific to the procedure to be performed and the relevant pre-operative diagnosis. For example, the patient data may indicate which joint the procedure will be performed on (e.g., right knee, left knee). The patient data may indicate a diagnosed deformity, for example indicating whether a knee joint was diagnosed as having a varus deformity or a valgus deformity. This or other data that may facilitate the surgical procedure may be obtained at step 402.

At step 404, a system setup, calibration, and registration workflow is provided, for example by the surgical system 200. The system setup, calibration, and registration workflows may be configured to prepare the surgical system 200 for use in facilitating a surgical procedure. For example, at step 404, the computing system 224 may operate to provide graphical user interfaces that include instructions for performing system setup, calibration, and registrations steps. The computing system 224 may also cause the tracking system 222 to collect tracking data and control the robotic device 220 to facilitate system setup, calibration, and/or registration. The computing system 224 may also receiving tracking data from the tracking system 222 and information from the computing system 224 and use the received information and data to calibrate the robotic device 220 and define various geometric relationships between tracked points (e.g., fiducials, markers), other components of the surgical system 200 (e.g., robotic arm 232, surgical device 234, probe), and virtual representations of anatomical features (e.g., virtual bone models).

The system setup workflow provided at step 404 may include guiding the robotic device 220 to a position relative to a surgical table and the patient which will be suitable for completing an entire surgical procedure without repositioning the robotic device 220. For example, the computing system 224 may generate and provide a graphical user interface configured to provide instructions for moving a portable cart of the robotic device 220 into a preferred position. In some embodiments, the robotic device 220 can be tracked to determine whether the robotic device 220 is properly positioned. Once the cart is positioned, in some embodiments the robotic device 220 is controlled to automatically position the robotic arm 232 in a pose suitable for initiation of calibration and/or registration workflows.

The calibration and registration workflows provided at step 404 may include generating instructions for a user to perform various calibration and registration tasks while operating the tracking system 222 to generate tracking data. The tracking data can then be used to calibrate the tracking system 222 and the robotic device 220 and to register the first fiducial tree 240, second fiducial tree 241, and third fiducial tree 242 relative to the patient's anatomical features, for example by defining geometric relationships between the fiducial trees 240-242 and relevant bones of the patient in the example of FIG. 2. The registration workflow may include tracking a probe used to touch various points on the bones of a joint. In some embodiments, providing the registration workflow may include providing instructions to couple a checkpoint (e.g., a screw or pin configured to be contacted by a probe) to a bone and tracking a probe as the probe contacts the checkpoint and as the probe is used to paint (e.g., move along, touch many points along) one or more surfaces of the bone. The probe can be moved and tracked in order to collect points in or proximate the joint to be operated upon as well as at other points on the bone (e.g., at ankle or hip for a knee surgery).

In some embodiments, providing the registration workflow includes generating instructions to move the patient's leg to facilitate collection of relevant tracking data that can be used to identify the location of a biomechanical feature, for example a hip center point. Providing the registration workflow can include providing audio or visual feedback indicating whether the leg was moved in the proper manner to collect sufficient tracking data. Various methods and approaches for registration and calibration can be used in various embodiments. Step 404 may include steps performed before or after an initial surgical incision is made in the patient's skin to initiate the surgical procedure.

At step 406, an initial assessment workflow is provided, for example by the surgical system 200. The initial assessment workflow provides an initial assessment of the joint to be operated upon based on tracked poses of the bones of the joint. For example, the initial assessment workflow may include tracking relative positions of a tibia and a femur using data from the tracking system while providing real-time visualizations of the tibia and femur via a graphical user interface. The computing system 224 may provide instructions via the graphical user interface to move the tibia and femur to different relative positions (e.g., different degrees of flexion) and to exert different forces on the joint (e.g., a varus or valgus force). In some embodiments, the initial assessment workflow includes determine, by the surgical system 200 and based on data from the tracking system 222, whether the patient's joint has a varus or valgus deformity, and, in some embodiments, determining a magnitude of the deformity. In some embodiments, the initial assessment workflow may include collecting data relating to native ligament tension or native gaps between bones of the joint. In some embodiments, the initial assessment workflow may include displaying instructions to exert a force on the patient's leg to place the joint in a corrected state corresponding to a desired outcome for a joint arthroplasty procedure, and recording the relative poses of the bones and other relevant measurements while the joint is in the corrected state. The initial assessment workflow thereby results in collection of data that may be useful for the surgical system 200 or a surgeon in later steps of process 400.

At step 408, an implant planning workflow is provided, for example by the surgical system 200. The implant planning workflow is configured to facilitate users in planning implant placement relative to the patient's bones and/or planning bone cuts or other modifications for preparing bones to receive implant components. Step 408 may include generating, for example by the computing system 224, three-dimensional computer models of the bones of the joint (e.g., a tibia model and a femur model) based on the segmented medical images received at step 402. Step 408 may also include obtaining three-dimensional computer models of prosthetic components to be implanted at the joint (e.g., a tibial implant model and a femoral implant model). A graphical user interface can be generated showing multiple views of the three-dimensional bone models with the three-dimensional implant models shown in planned positions relative to the three-dimensional bone models. Providing the implant planning workflow can include enabling the user to adjust the position and orientation of the implant models relative to the bone models. Planned cuts for preparing the bones to allow the implants to be implanted at the planned positions can then be automatically based on the positioning of the implant models relative to the bone models.

The graphical user interface can include data and measurements from pre-operative patient data (e.g., from step 402) and from the initial assessment workflow (step 406) and/or related measurements that would result from the planned implant placement. The planned measurements (e.g., planned gaps, planned varus/valgus angles, etc.) can be calculated based in part on data collected via the tracking system 222 in other phases of process 400, for example from initial assessment in step 406 or trialing or tensioning workflows described below with reference to step 412.

The implant planning workflow may also include providing warnings (alerts, notifications) to users when an implant plan violates various criteria. In some cases, the criteria can be predefined, for example related to regulatory or system requirements that are constant for all surgeons and/or for all patients. In other embodiments, the criteria may be related to surgeon preferences, such that the criteria for triggering a warning can be different for different surgeons. In some cases, the computing system 224 can prevent the process 400 from moving out of the implant planning workflow when one or more of certain criteria are not met.

The implant planning workflow provided at step 408 thereby results in planned cuts for preparing a joint to receive prosthetic implant components. In some embodiments, the planned cuts include a planar tibial cut and multiple planar femoral cuts, for example as described above with reference to FIG. 1. The planned cuts can be defined relative to the virtual bone models used in the implant planning workflow at step 408. Based on registration processes from step 404 which define a relationship between tracked fiducial markers and the virtual bone models, the positions and orientations of the planned cuts can also be defined relative to the tracked fiducial markers, (e.g., in a coordinate system used by the tracking system 222). The surgical system 200 is thereby configured to associate the planned cuts output from step 408 with corresponding planes or other geometries in real space.

At step 410, a bone preparation workflow is provided, for example by the surgical system 200. The bone preparation workflow includes guiding execution of one or more cuts or other bone modifications based on the surgical plan created at step 408. For example, as explained in detail above with reference to FIGS. 2-3, the bone preparation workflow may include providing haptic feedback which constrains the surgical device 234 to a plane associated with a planned cut to facilitate use of the surgical device 234 to make that planned cut. In other embodiments, the bone preparation workflow can include automatically controlling the robotic device 220 to autonomously make one or more cuts or other bone modifications to carry out the surgical plan created at step 408. In other embodiments, the bone preparation workflow comprises causing the robotic device 220 to hold a cutting guide, drill guide, jig, etc. in a substantially fixed position that allows a separate surgical device to be used to execute the planned cut while being confined by the cutting guide, drill guide, jig, etc. The bone preparation workflow can thus include control of a robotic device in accordance with the surgical plan.

The bone preparation workflow at step 410 can also include displaying graphical user interface elements configured to guide a surgeon in completing one or more planned cuts. For example, the bone preparation workflow can include tracking the position of a surgical device relative to a plane or other geometry associated with a planned cut and relative to the bone to be cut. In this example, the bone preparation workflow can include displaying, in real-time, the relative positions of the surgical device, cut plane or other geometry, and bone model. In some embodiments, visual, audio, or haptic warnings can be provided to indicate completion or start of an event or step of the procedure, entry or exit from a state or virtual object, interruptions to performance of the planned cut, deviation from the planned cut, or violation of other criteria relating to the bone preparation workflow.

In some embodiments, step 410 is provided until all bone cuts planned at step 408 are complete and the bones are ready to be coupled to the implant components. In other embodiments, for example as shown in FIG. 4, a first iteration of step 410 can include performing only a portion of the planned cuts. For example, in a total knee arthroplasty procedure, a first iteration of step 410 can include making a tibial cut to provide a planar surface on the tibia without modifying the femur in the first iteration of step 410.

Following an iteration of the bone preparation workflow at step 410, the process 400 can proceed to step 412. At step 412 a mid-resection tensioning workflow or a trialing workflow is provided, for example by the surgical system 200. The mid-resection tensioning workflow is provided when less than all of the bone resection has been completed. The trialing workflow is provided when all resections have been made and/or bones are otherwise prepared to be temporarily coupled to trial implants. The mid-resection tensioning workflow and the trialing workflow at step 412 provide for collection of intraoperative data relating to relative positions of bones of the joint using the tracking system 222 including performing gap measurements or other tensioning procedures that can facilitate soft tissue balancing and/or adjustments to the surgical plan.

For example, step 412 may include displaying instructions to a user to move the joint through a range of motion, for example from flexion to extension, while the tracking system 222 tracks the bones. In some embodiments, gap distances between bones are determined from data collected by the tracking system 222 as a surgeon places the joint in both flexion and extension. In some embodiments, soft tissue tension or distraction forces are measured. Because one or more bone resections have been made before step 412 and soft tissue has been affected by the procedure, the mechanics of the joint may be different than during the initial assessment workflow of step 402 and relative to when the pre-operative imaging was performed. Accordingly, providing for intra-operative measurements in step 412 can provide information to a surgeon and to the surgical system 200 that was not available pre-operatively and which can be used to help fine tune the surgical plan.

From step 412, the process 400 returns to step 408 to provide the implant planning workflow again, now augmented with data collected during a mid-resection or trialing workflow at step 412. For example, planned gaps between implants can be calculated based on the intraoperative measurements collected at step 414, the planned position of a tibial implant relative to a tibia, and the planned position of a femoral implant relative to a femur. The planned gap values can then be displayed in an implant planning interface during step 408 to allow a surgeon to adjust the planned implant positions based on the calculated gap values. In various embodiments, a second iteration of step 408 to provide the implant planning workflow incorporates various data from step 412 in order to facilitate a surgeon in modifying and fine-tuning the surgical plan intraoperatively.

Steps 408, 410, and 412 can be performed multiple times to provide for intra-operative updates to the surgical plan based on intraoperative measurements collected between bone resections. For example, in some cases, a first iteration of steps 408, 410, and 412 includes planning a tibial cut in step 408, executing the planned tibial cut in step 410, and providing a mid-resection tensioning workflow in step 414. In this example, a second iteration of steps 408, 410, and 412 can include planning femoral cuts using data collected in the mid-resection tensioning workflow in step 408, executing the femoral cuts in step 410, and providing a trialing workflow in step 412. Providing the trialing workflow can include displaying instructions relating to placing trial implants on the prepared bone surfaces, and, in some embodiments, verifying that the trial implants are positioned in planned positions using the tracking system 222. Tracking data can be collected in a trialing workflow in step 412 relating to whether the trial implants are placed in acceptable positions or whether further adjustments to the surgical plan are needed by cycling back to step 408 and making further bone modifications in another iteration of step 410.

In some embodiments, executing process 400 can include providing users with options to jump between steps of the process 400 to enter a desired workflow. For example, a user can be allowed to switch between implant planning and bone preparation on demand. In other embodiments, executing process 400 can include ensuring that a particular sequence of steps of process 400 are followed. In various embodiments, any number of iterations of the various steps can be performed until a surgeon is satisfied that the bones have been properly prepared to receive implant components in clinically-appropriate positions.

As shown in FIG. 4, the process 400 includes step 414 where implantation of prosthetic components is facilitated. Once the bones have been prepared via step 410, the prosthetic components can be implanted. In some embodiments, step 414 is executed by the surgical system 200 by removing the robotic arm 232 from the surgical field and otherwise getting out of the way to allow a surgeon to fix the prosthetic components onto the bones without further assistance from the surgical system 200. In some embodiments, step 414 includes displaying instructions and/or navigational information that supports a surgeon in placing prosthetic components in the planned positions. In yet other embodiments, step 414 includes controlling the robotic arm 232 to place one or more prosthetic components in planned positions (e.g., holding a prosthetic component in the planned position while cement cures, while screws are inserted, constraining an impaction device to planned trajectory). Process 400 can thereby result in prosthetic components being affixed to modified bones according to an intra-operatively updated surgical plan.

Figure 5:
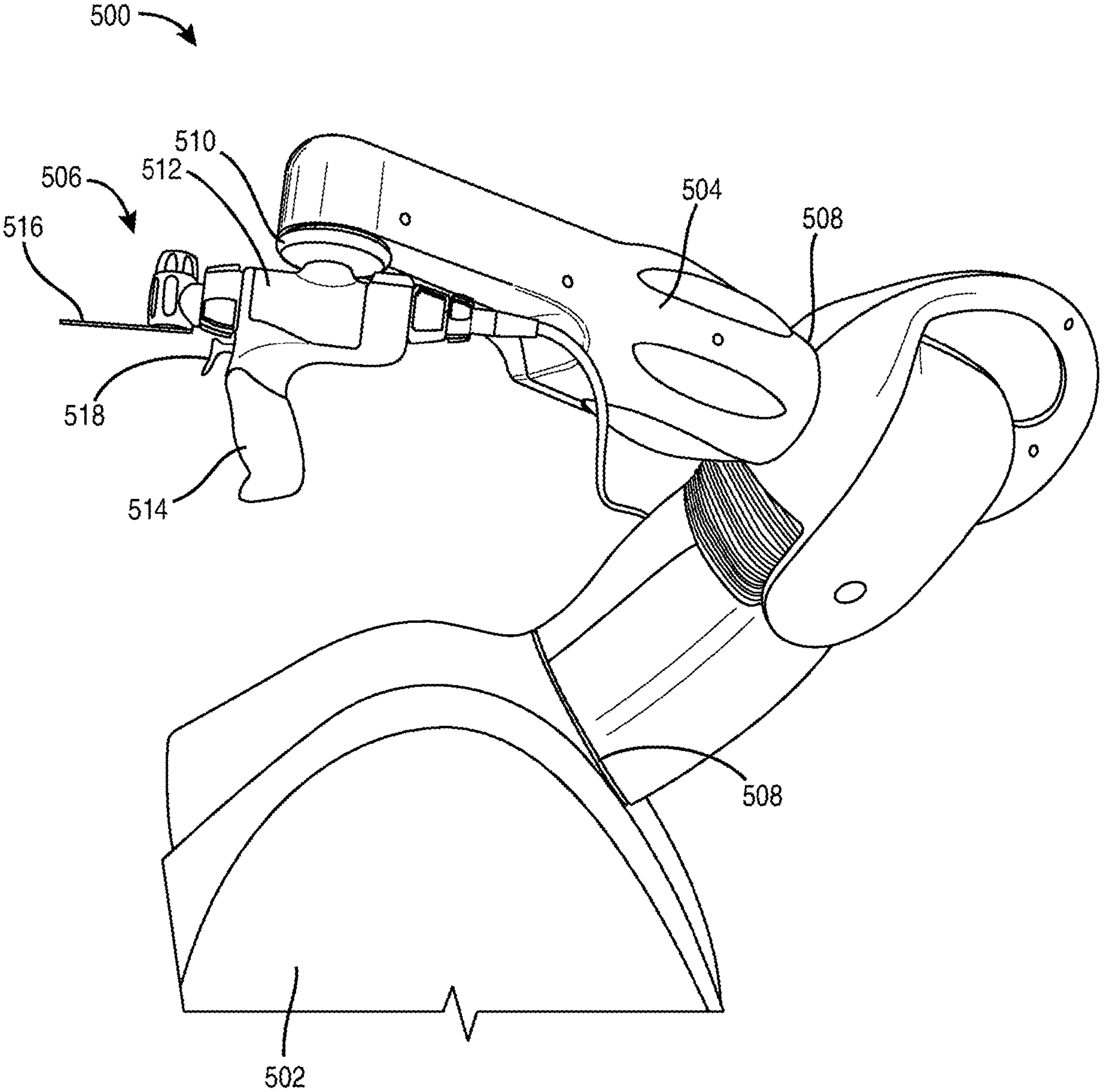
FIG. 5 is an illustration of a robotic device, according to an exemplary embodiment.

Referring now to FIG. 5, a robotic device 500 is shown, according to an exemplary embodiment. In general, the robotic device 500 is configured to modify a patient's anatomy (e.g., femur, tibia, etc.). Robotic device 500 may be an exemplary embodiment of the robotic device 220 as shown in FIG. 2, and may be part of surgical system 200 as shown in FIG. 2. The robotic device 500 includes a base 502, a robotic arm 504, and a surgical device 506. The robotic device 500 may be communicably coupled to a tracking system and a computing system (e.g., tracking system 222 and computing system 224).

The base 502 provides a moveable foundation for robotic arm 504, allowing the robotic arm 504 and the surgical device 506 to be positioned and repositioned as needed relative to a patient. The base 502 may also contain power systems, computing elements, motors, and other electronic or mechanical systems necessary for the functions of the robotic arm 504 and the surgical device 506 described below.

As described above in reference to the robotic device 220 in FIG. 2, the robotic arm 504 is configured to support the surgical device 506 and provide a force as instructed by a computing system (e.g., computing system 224). In some embodiments, the robotic arm 504 allows a user to manipulate the surgical device 506 and provides force feedback to the user. In such an embodiment, the robotic arm 504 includes joints 508 and a mount 510 that includes motors, actuators, or other mechanisms configured to allow a user to freely translate and rotate the robotic arm 504 and surgical device 506 through allowable poses while providing feedback to constrain or prevent some movements of the robotic arm 504 and surgical device 506 as instructed by the computing system 224. In some embodiments, the robotic arm 504 is configured to move the surgical device 506 to a new pose automatically, without direct user manipulation, as instructed by computing system 224 in order to position the robotic arm 504 as desired and/or to complete certain surgical tasks, including modifications to a patient's anatomy (e.g., femur, tibia, etc.).

In some embodiments, the surgical device 506 is configured to cut, burr, grind, drill, partially resect, reshape, and/or otherwise modify a bone. The surgical device 506 may also include a holding arm or other support configured to hold an implant (e.g., acetabular cup, implant augment, etc.), or an impaction tool configured to provide impaction force to a cup implant. The surgical device 506 may also be, or include, any suitable cutting tool (e.g., a drill with a rotary bit, a drill with a spherical burr, a sagittal saw, a sagittal saw blade, a laser cutting device, etc.), and may be, or include, one of multiple tools interchangeably connected to the robotic device 500. For example, as shown in FIG. 5 the surgical device 506 may be a sagittal saw, comprising a housing 512, a handle 514, a sagittal saw blade 516, and a trigger mechanism 518. The housing 512 may be interchangeably connected to mount 510, and may be configured to support the handle 514, sagittal saw blade 516, and trigger mechanism 518. The housing 512 may also contain power systems, computing elements, motors, and other electronic or mechanical systems necessary for the functions of the surgical device 506. The handle 514 may extend from housing 512, and may be configured to allow the user to manipulate the surgical device 506. The handle 514 may be made of any material suitable for cleaning or sterilization. The sagittal saw blade 516 may be interchangeably connected to the housing 512, and may be aligned parallel with the housing 512, or perpendicular to the housing 512 axis. Trigger mechanism 518 may be connected to the housing 512, and can be configured to be pressed (depressed), released, held in place, double-pressed (e.g., pressed, released, and then pressed again in quick succession (e.g., within one second)), or any combination thereof. The trigger mechanism 518 may also be made of any material suitable for cleaning or sterilization, and may interact with the electronic or mechanical systems necessary for the functions of the surgical device 506 located in the housing 512.

Robot Control with Dynamic Resection Combination

Figure 6:
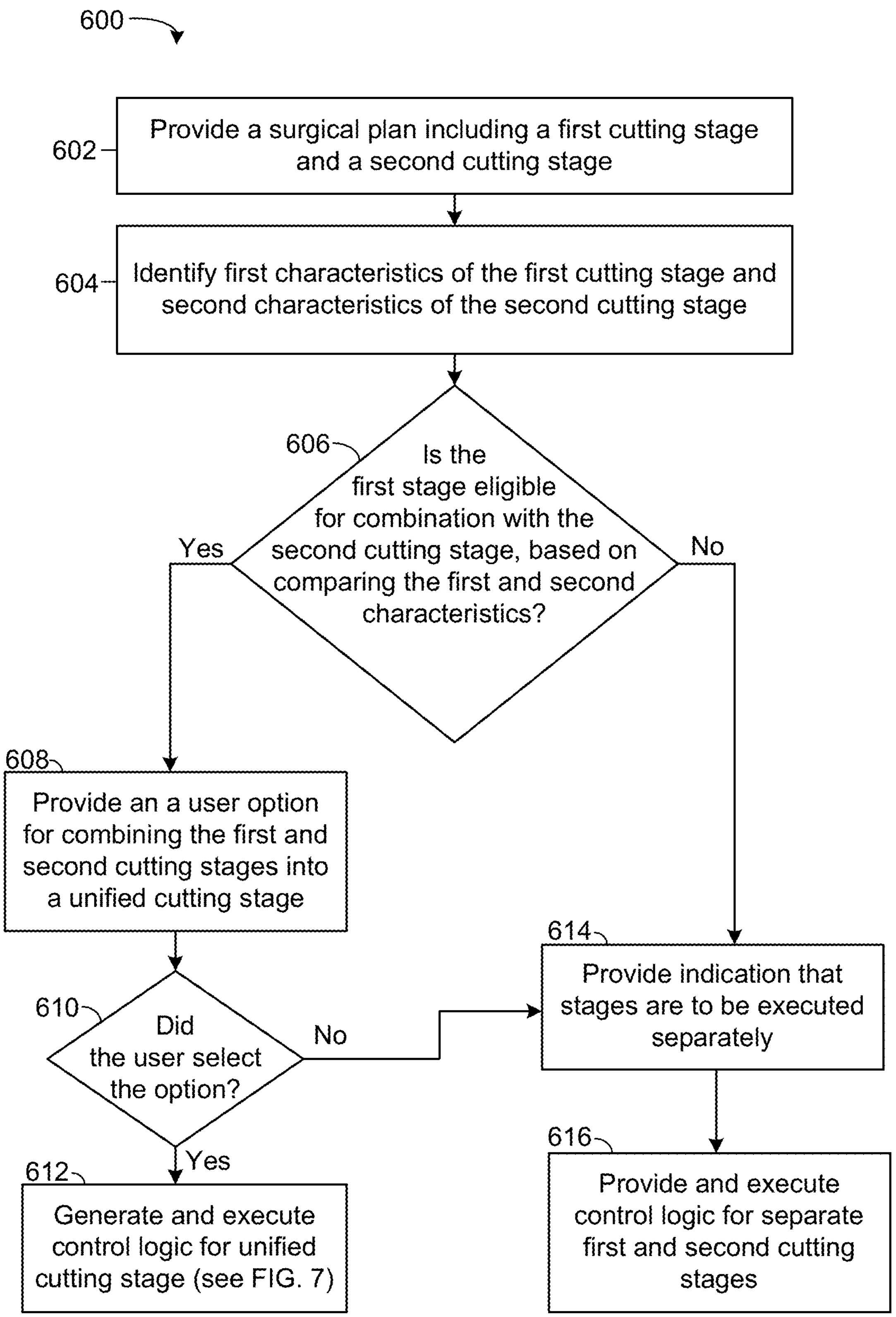
FIG. 6 is a flowchart of a process of controlling a surgical robot, according to some embodiments.

Referring now to FIG. 6, a flowchart of a process 600 of operating a robotically-assisted surgical system is shown, according to some embodiments. Process 600 can be executed by surgical system 200, for example by computing system 224 and/or combination of computing components, robot controllers, processors, etc. as may be included in various robotically-assisted surgical systems. Process 600 can be executed to control robotic device 500 of FIG. 5, for example. Process 600 can be executed as implemented as part of and/or using process 300 and/or process 400, for example in the bone preparation workflow of step 410 of process 400.

At step 602, a surgical plan is provided. The surgical plan includes a first cutting stage and a second cutting stage. The first cutting stage and the second cutting stage can indicate different regions of bone for resection, for example a first region and a second region on the same bone, a first region on a first bone and a second region on a second bone, etc. The first cutting stage and the second cutting stage can each be associated with a planar cut of the multiple planar cuts illustrated in FIG. 1 and described above, or the first cutting stage can include preparing one or more planar surfaces and the second cutting stage can include preparing for one or more pilot holes or other recesses (e.g., pilot holes 120 as in FIG. 1), according to various embodiments. In various embodiments, the surgical plan is associated with an arthroplasty operation for example for total, partial, and/or revision knee, hip, or shoulder replacement, with spine surgery operations, with neurosurgical operations, with foot, hand, or ankle operations, with orthopaedic trauma repair operations, etc. in various embodiments.

While reference is made to cutting stages, the teachings herein can be adapted to other surgical or medical intervention stages in various embodiments (e.g., implant installation stages, impaction stages, irrigation stages, debridement stages, ablation stages, radiation therapy stages, soft tissue manipulation stages, suturing stages, medication delivery stages, etc., in various embodiments). Furthermore, while the discussion herein refers to a “first” stage and a “second” stage, such labels are provided to differentiate procedural stages and a surgical plan within the scope of the present disclosure can include any number of cutting stages from which the first stage and the second stage can be selected in any combination or order (e.g., with other stages before, after, and/or between the first stage and the second stage) (e.g., user selected and/or automatically selected based on characteristics of such stages). Furthermore, teachings herein relating to two stages (e.g., first and second as referred to herein) can be extended to embodiments with any higher number of stages as may be included for a surgical plan, selected by a user, or otherwise determined as compatible with the various teachings herein (e.g., a first, second, third, fourth, etc. cutting stage treated as described for first and second stages herein).

At step 604, first characteristics of the first cutting stage and second characteristics of the second cutting stage are identified. The characteristics of each cutting stage can include any one or more of any of the following: a cut size (e.g., bone volume to removed, distance to be traversed to complete a cut), a tissue type (e.g., bone v. soft tissue), name of anatomical structure to be cut (e.g., tibia, femur, acetabulum, glenoid, vertebra, etc.), type of cutting stage (e.g., planar resection, drill hole resection, curved surface resection, etc.), an associated implant component (e.g., acctabular cup, femoral component, femoral stem, tibial component, augment, portion of a modular implant, glenoid component, humeral component, spinal plate, spinal fusion implant, bone pin or plate, etc.), identity of tool(s) compatible with the cutting stage (e.g., usable to complete the cutting stage), an indication of whether autonomous execution is an option (e.g., based on regulatory approval, based on cut geometry), an indication of joint flexion requirements for the cutting stage (e.g., a range of flexion angles the joint should be in for execution of the cutting stage), an incision position associated with the cutting stage (e.g., where an incision, retraction, etc. should be placed to allow access to anatomy being cut in the cutting stage), an irrigation requirement (e.g., whether irrigation is required, desired, undesirable, etc. for a cutting stage), or various other potential characteristics descriptive of features of a cutting stage. The characteristics of each cutting stage can be based on the surgical plan provided in step 602, for example including positional data associated with resections to be executed in each cutting stage, shapes and/or positions of haptic objects or other control geometries associated with cutting stages, etc. in various embodiments. In some embodiments, characteristics of the first cutting stage and the second cutting stage are retrieved from a database, look-up table, etc. based on the surgical plan and/or otherwise derived from the surgical plan using, for example, various rules-based calculations or machine-learnt classification algorithms. First characteristics descriptive of the first cutting stage and second characteristics descriptive of the second cutting stage can thereby be identified in step 604.

At step 606, a determination is made with respect to whether the first cutting stage is eligible for combination with the second cutting stage based on comparing the first characteristics and the second characteristics. Comparing the first characteristics with the second characteristics provides a determination as to whether the first stage is combinable with the second stage, i.e., whether the first cutting stage and the second cutting stage can be provided as a unified cutting stage rather than sequential, distinct cutting stages.

In some embodiments, different types of characteristics can be compared according to different criteria, for example criteria relating to whether the characteristics match, overlap (e.g., partially overlap), oppose one another; whether the characteristics are within a threshold difference of one another or differ by more than a threshold amount; whether a function using the characteristics as an inputs has an output above or below a threshold, etc. In some embodiments, a sequence of comparisons is performed, for example checking the first characteristics against the second characteristics in a predefined order, an order resulting from following a logic flow through a flowchart, and/or based on various if/then rules. Based on satisfaction (or lack of satisfaction) of various criteria resulting from comparing the characteristics, a determination can be output as to whether the first cutting stage is combinable with the second cutting stage. In some embodiments, a multi-dimensional array (look-up table, etc.) is preset (e.g., in factory production, prior to any particular surgical planning for a particular patient) which indicates whether the first and second cutting stages are combinable for many (e.g., all) possible sets of combinations of first characteristics and second characteristics, and is used in step 606 as a look-up table to select a determination as to whether the first cutting stage is eligible for combination with the second cutting stage.

If a determination is made that the first cutting stage is eligible for combination with the second cutting stage (“Yes” at step 608), process 600 proceeds to step 608 where a user option is provided for selecting whether to combine the first and second cutting stages into a unified cutting stage. The user option can be provided as a selectable button, icon, input field, etc. of a graphical user interface, for example a graphical user interface presented on display 264 as in FIG. 2, a graphical user interface presented on a personal computing device (e.g., laptop or desktop computer, etc.).

The user option can be provided in step 608 together with a variety of additional information relating to the option, for example information facilitating a comparison between providing the unified cutting stage and providing the first and second cutting stages sequentially. Such information can include characteristics of the first and second cutting stages (e.g., as identified in step 604) and characteristics of the unified cutting stage (e.g., based on results of comparisons performed in step 606). For example, the user option can be provided with an indication of tool(s) which can be used in the unified cutting stage, an indication of whether automation execution is available for the unified cutting stage, a time estimate for completing the unified cutting stage, and, in some embodiments, corresponding information for providing the first and second cutting stages sequentially. The user is thereby provided with relevant information relating to comparisons between the unified cutting stage and the first and second cutting stages, which can facilitate the user in determining whether to select the user option. A surgeon, for example, can thereby make a decision as to whether to unify cutting stages classified as eligible for combination based on information provided with the option and in view of the surgeon's personal preferences, clinical knowledge relating to a particular patient, and/or other relevant considerations.

At step 610, a determination is made as to whether the user selected the option to unify the first and second cutting stages (In some embodiments, process 600 combines cutting stages automatically—i.e., defaults to "Yes" at step 610). If the user selected the option ("Yes" at step 610), the process 600 proceeds to step 612 where control logic for a unified cutting stage is generated and executed. Step 612 can include controlling a robotic device (e.g., robotic device 500, robotic arm, handheld robotic instrument, etc.) using unified control logic. Step 612 can include combining first control logic associated with the first cutting stage with second control logic associated with the second cutting stage to provide unified control logic, in some embodiments. In some embodiments, step 612 is provided by executing process 700 of FIG. 7, described in detail below. Step 612 can include causing execution of the unified cutting stage to modify one or more anatomical structures (e.g., one or more bones) to provide a result (e.g., bone modification, resection, etc.) consistent with a plan for the first and second cutting stages, while abstaining from an interruption that may occur between the first cutting stage and second cutting stages if executed sequentially (e.g., as compared to step 616 described below). For example, execution of step 612 can include resecting portions of one or more bones associated with the first and second cutting stages in any order, for example such that the unified cutting stages alternates between resecting first portions associated with the first cutting stage and second portions of the second cutting stage (e.g., such that at least one portion associated with the first cutting stage is resected after at least one portion associated with the second cutting stage and vice versa). A unified cutting stage can thereby be executed in step 612.

If the first stage is not eligible for combination with the second cutting stage ("No" at step 606) or the user declines (does not select) the option to combine the cutting stages ("No" at step 610), process 600 proceeds to step 614 where an indication is provided that stages are to be executed separately. The indication can be provided via a graphical user interface, a graphical user interface, for example a graphical user interface presented on display 264 as in FIG. 2, a graphical user interface presented on a personal computing device (e.g., laptop or desktop computer, etc.).

The indication can be provided with additional selectable options, adjustable settings, etc. associated with separately providing the first and second cutting stages (e.g., based on the characteristics identified in step 604). For example, options can be presented with respect to user selection of tool(s) suitable for use in executing the first cutting stage and/or the second cutting stage, user selection of whether automated execution should be provided, and/or other preferences or selections, according to various embodiments. Time estimates for completing surgical steps according to the various selectable options can also be provided in step 614, for example estimated automatically based on tool size, cutting rate, bone density, and/or resection size for the first cutting stage and/or the second cutting stage. A surgeon or other user can thereby be provided with relevant information which facilitates user selection of options for how the first and second cutting stages will be controlled and executed.

At step 616, control logic is provided and executed for separate (sequential, etc.) first and second cutting stages. Step 616 can include executing the first cutting stage using first control logic, determining completion of the first cutting stage, switching to second control logic in response to completion of the first cutting stage, and executing the second cutting stage using the second control logic. Sequentially executing the first control logic followed by the second control logic can include controlling a robotic device (e.g., robotic device 500, robotic arm, handheld robotic instrument, etc.) using the first control logic, followed by the second control logic. Control of the robotic device can be interrupted between the first and second cutting stages. In some embodiments and scenarios, the first control logic causes the robotic device to provide force feedback to constrain a surgical tool to a haptic object for execution of the first cutting stage, while the second control logic causes automated movement of the robotic device through a control path for execution of the second cutting stage (or vice versa).

In some embodiments and scenarios, different tools are used in the first cutting stage and the second cutting stage, with a user prompted to detach a first tool and attach a second tool between the first cutting stage and the second cutting stage (e.g., to switch from a saw for the first cutting stage to a burr for the second cutting stage, to switch from a reamer for the first cutting stage to a burr for the second cutting stage, to switch from a burr for the first cutting stage to a saw or reamer for the second cutting stage, to change between sizes of burr, reamer, or saw between cutting stages, etc.). Other adjustments or checks may be made between the first and second cutting stages, for example based on characteristics of the first and second cutting stages identified in step 606, for example patient repositioning (e.g., adjustment of joint flexion), a change in retraction or incision, starting or stopping of irrigation, confirmation of registration of a tracking system, intraoperative imaging, etc. in various embodiments and depending on various characteristics of the first and second cutting stages.

Process 600 can thereby adaptively implement (e.g., guide, control, execute, etc.) a surgical plan including a planned first cutting stage and a planned second cutting stage by generating and executing unified control logic for a unified cutting stage and/or separate control logic for sequential first and second cutting stages based on characteristics of the cutting stages (i.e., based on the surgical plan).

Figure 7:
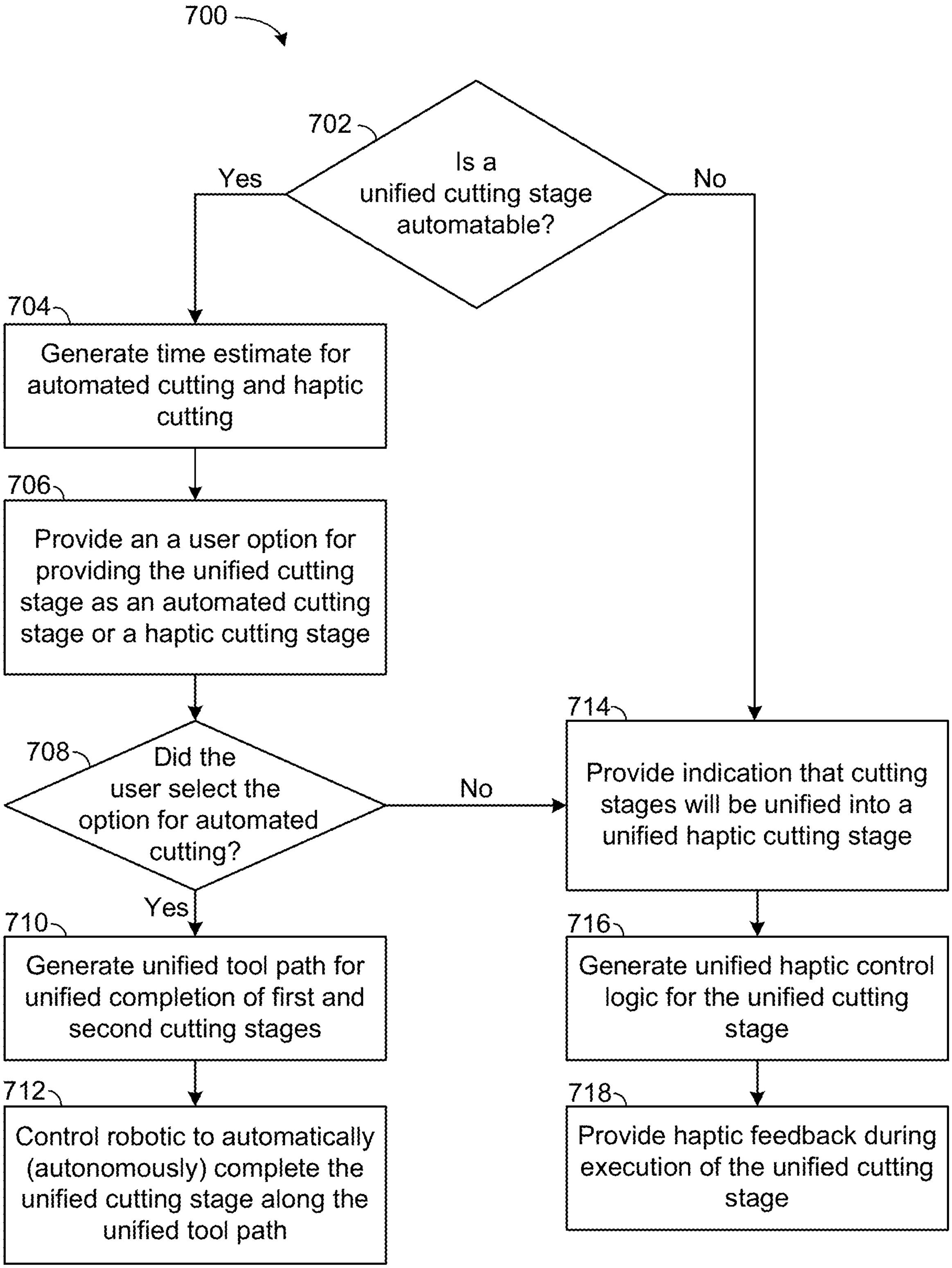
FIG. 7 is a flowchart of a process of controlling a surgical robot, according to some embodiments.

Referring now to FIG. 7, a process 700 for controlling a robotic device (e.g., robotic device 500) is shown, according to some embodiments. Process 700 can be executed by surgical system 200, for example by computing system 224 and/or combination of computing components, robot controllers, processors, etc. as may be included in various robotically-assisted surgical systems. Process 700 can be executed to control robotic device 500 of FIG. 5, for example. Process 700 can be executed as implemented as part of and/or using process 300 and/or process 400, for example in the bone preparation workflow of step 410 of process 400. In the embodiment shown, process 700 is executed as part of step 612 of process 600. Process 700 can also be adapted to provide step steps 614 and 614 of process 600, can be executed independently of process 600, or otherwise deployed as may be suitable in various embodiments.

At step 702, a determination is made as to whether a unified cutting stage is automatable. Step 702 can include performing one or more assessments of the unified cutting stage. In some embodiments, an assessment of the unified cutting stage can include checking whether the first cutting stage and the second cutting stage are eligible for automation (e.g., based on characteristics relating thereto identified in step 604 of process 600, based on regulatory approval of automation for the first and second cutting stages) and determining that the unified cutting stage passes the assessment if both the first and second cutting stages are automatable and fails the assessment if either or both of the first cutting stage or the second cutting stage is ineligible for automation. In some embodiments, an assessment of the unified cutting stage can including determining an overall shape of the unified cutting stage and comparing the overall shape to a criterion, for example determining whether the unified cutting stage meets a convexity criterion, convexity criterion, can be represented by a predefined set of shapes usable in automation control logic, etc. in various embodiments. In some embodiments, an assessment of the unified cutting stage is based on bone density of bone to be resected in the unified cutting stage, whereby automated cutting may be available or unavailable above or below a threshold bone density value in various embodiments. Various assessments of the unified cutting stages can be used in the step 702 to determine, based on one or more of various such assessments, whether the unified cutting stage is automatable in 702.

If the unified cutting stage is determined to be automatable in step 702, the process 700 proceeds to step 704 where time estimates are provided for different control options, for example a first time estimate for automated execution of the unified cutting stage and a second time estimate for executing the unified cutting stage with haptic feedback provided on constrained manual cutting with a robotic device (e.g., robotic device 500). The time estimates indicate the duration (amount) of time expected for completion of the unified cutting stage under different control options and based on a particular surgical plan. In some embodiments, generating the time estimates includes estimating a tool path for an automated unified cutting stage, determining a length of the tool path, estimating a speed along the tool path (e.g., based on bone density to be encountered by the tool along the tool path, based on cutting rate of a selected tool, based on curvature of the tool path, etc.), and estimating a duration to complete the cut based on the estimated length and speed. In some embodiments, generating the time estimates can include predicting, using a model trained on prior surgical operations, a duration of time for manual cutting while constrained by a haptic boundary, for example using a three-dimensional representation of the resection to be completed as an input to the model (e.g., machine-learning model trained on measured durations of cuts in previous operations or experiments together with associated representations of resections to be completed in such operations). Various such techniques for generating time estimates for automated and/or haptic cutting stages can be provided in various embodiments.

At step 706, a user option for selecting whether to provide the unified cutting stage as an automated cutting stage or as a haptic cutting stage is provided. The user option can be provided in a graphical user interface, for example via display 264 as in FIG. 2 and/or a graphical user interface presented on a personal computing device (e.g., laptop or desktop computer, etc.). The graphical user interface can include the time estimates generate in step 704, such that the graphical user interface shows a first time estimation for automating the unified cutting stage and a second time estimation for providing a haptic cutting stage. A user can then make a selection to provide the unified cutting stage as an automated cutting stage or as a haptic cutting stage based on such time estimates, for example to select the faster or slower option depending upon surgeon preferences. In some embodiments, process 700 automatically selects and/or otherwise defaults to selection of the option associated with the shortest time estimate (i.e., selects automation if predicted to be faster than haptic execution; selects haptic execution if expected to be faster than automated execution). Such features can decrease overall resection time, which can have clinical benefits associated with reduced operation time for patients as well as operational benefits for healthcare staff, facilities, and equipment, and/or otherwise enable a surgeon or other healthcare decisionmaker to balance resection duration with other clinical considerations for treatment of a particular patient.

At step 708, a determination is made as to whether the user selected the option for automated cutting. If a user selected automation of the unified cutting stage ("Yes" at step 708), process 700 proceeds to step 710 where a unified tool path for unified completion of the first and second cutting stages is generated. The unified tool path can be generated using various path planning algorithms in various embodiments, for example to maximize cut quality, cut speed, and/or various other parameters, to complete resection of a region associated with the unified cutting stage. Path planning can be provided independent of any consideration of association of the first or second cutting stage with different portions of a unified cutting region, i.e., such that the path planning is agnostic of the fact that the unified cutting path is based on unification of first and second cutting stages. Accordingly, in some scenarios, the unified tool path will repeatedly switch between intersecting a region associated with the first cutting stage and intersecting a region associated with the second cutting stage, as may be optimal for completing resection of the combination of such regions.

At step 712, a robot (e.g., robotic device 500) is controlled to automatically (autonomously) to complete the unified cutting stage along the unified tool path. In step 712, the robot is controlled to move a cutting tool along the unified tool path determined in step 710. The unified cutting stage is thereby executed in step 712.

If the user selects haptic cutting (i.e., selects against automating the unified cutting stage) ("No" at step 7048), or if the unified cutting stage is determined to be non-automatable ("No" at step 702), process 700 proceeds to step 714.

At step 714, an indication is provided that the cutting stages will be unified into a unified haptic cutting stage. The indication can be provided via graphical user interface, for example via display 264 as in FIG. 2 and/or a graphical user interface presented on a personal computing device (e.g., laptop or desktop computer, etc.). The graphical user interface can also provide various additional visualizations, information, three-dimensional representations, options (e.g., tool selection options), etc. associated with the unified haptic cutting stage. In some embodiments, the user can also select manual cutting mode (e.g., no robotic feedback or automation), a navigated mode (e.g., visual feedback only), or other type of robotic, navigated, or non-navigated mode as may be eligible to be performed according to determinations adapted from the teachings herein.

At step 716, unified haptic control logic is generated for the unified cutting stage. Step 716 can be implemented using process 900 of FIG. 9, in some embodiments. In some embodiments, generating the unified haptic control logic includes generating a unified haptic object, for example a single continuous haptic boundary extending across regions associated with both the first cutting stage and the second cutting stage. In some embodiments, generating the unified haptic control logic may include providing control logic for using both a first haptic object associated with the first cutting stage and a second haptic object associated with the second haptic object in a unified manner, for example by generating logic for dynamically selecting between the first haptic object and the second haptic object for calculation of force feedback and/or by generating third haptic object for connecting the first haptic object with the second haptic object (e.g., for providing a pathway between the first and second haptic objects). Accordingly, unified haptic control logic can be generated in step 716.

At step 718, haptic feedback is provided during execution of the unified cutting stage. Step 718 can include controlling a robot (e.g., robotic device 500) to provide force feedback to a user to constrain a cutting tool (or other surgical end effector) to a unified haptic boundary and/or otherwise to at least a combination of a first haptic boundary and a second haptic boundary. The user can manually move the cutting tool through space within the boundary or boundaries to complete the unified cutting stage. Haptic feedback can be provided in step 718 using techniques described above with reference to FIGS. 2-5 above, according to various embodiments.

Process 700 can thereby generate and execute control logic for providing the unified cutting stage as an automated unified cutting stage or a haptic unified cutting stage, for example as determined based on criteria for evaluating automatability of the unified cutting stage and/or user selection between automation and haptic guidance. Process 700 can also be adapted for providing user selection between automation and haptic guidance for execution of separate, sequential first and second cutting stage, for example in step 616 of process 600. Process 700 can be executed before the unified cutting stage is initiated and/or during the unified cutting stage, for example such that a user can select between, switch between, etc. automated and haptic execution (and/or manual, navigated, etc. modes) during execution of a cutting stage, in various embodiments.

Figure 8:
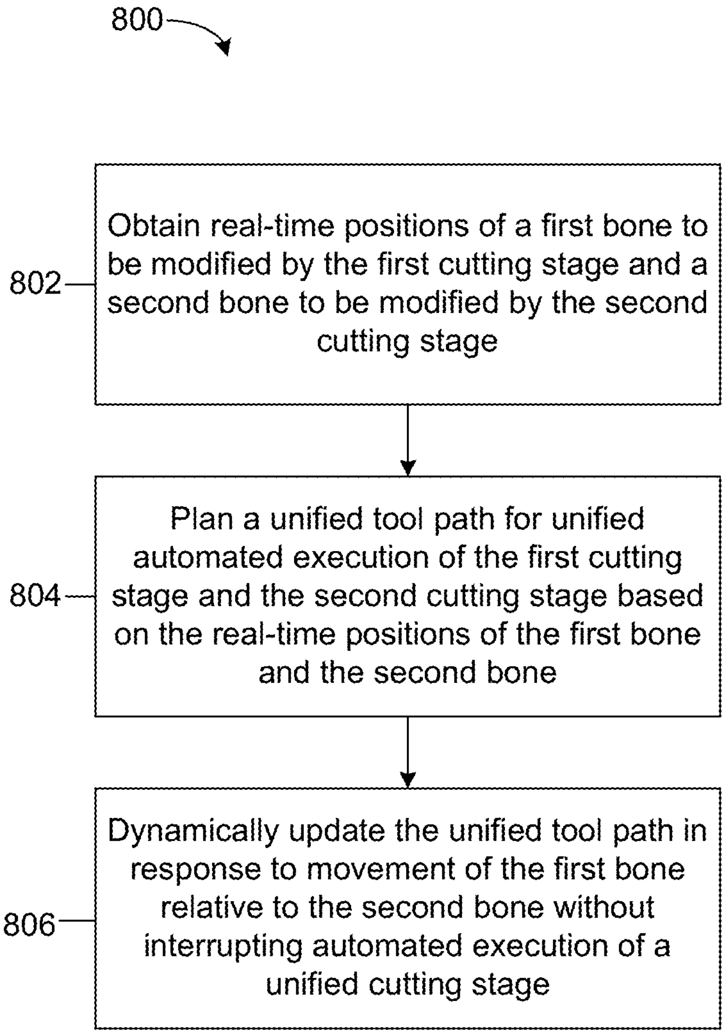
FIG. 8 is a flowchart of a process of controlling a surgical robot, according to some embodiments.

Referring now to FIG. 8, a process 800 for dynamically providing an automated unified cutting stage is shown, according to some embodiments. Process 800 can be provided as part of steps 710 and 712 of process 700, for example as part of step 612 of process 600. Process 800 can be executed by surgical system 200, for example by computing system 224 and/or combination of computing components, robot controllers, processors, etc. as may be included in various robotically-assisted surgical systems. Process 800 can be executed to control robotic device 500 of FIG. 5, for example. Process 800 can be executed as implemented as part of and/or using process 300 and/or process 400, for example in the bone preparation workflow of step 410 of process 400.

At step 802, real-time positions of a first bone and a second bone are obtained. A surgical plan include a first cutting stage for modifying the first bone and a second cutting stage for modifying the second bone, with the first cutting stage and the second cutting stage selected for unification and automated execution, for example via process 600 and/or process 700. The real-time positions of the first bone and the second bone can be obtained by optically tracking at least one first marker coupled to the first bone and at least one second marker coupled to the second bone (e.g., fiducial trees 240 and 241 as in FIG. 2), for example using an optical tracking system 222 as in FIG. 2, and/or otherwise tracked using another tracking modality (e.g., mechanical tracking, electromagnetic tracking, image processing, etc.). Step 802 can include dynamically updating relative positions of virtual models of the first bone and the second bone in a virtual modeling coordinate system based on tracked relative movement of the first bone and the second bone.

At step 804, a unified tool path is planned for unified automated execution of the first cutting stage and the second cutting stage based on the real-time positions of the first bone and the second bone. The unified tool path is planned to intersect portions of the first bone to be resected and portions of the second bone to be resected; accordingly, the unified tool path also includes transition segments for movement of the tool between the first bone and the second bone. Such space between the bones to be traversed as part of the unified tool path can be determined based on the tracked relative bone positions from step 802. Step 804 can then include path planning (e.g., using one or more of various techniques for optimizing tool path) to determine a tool path expected to complete a unified resection of regions of both the first and second bones while accounting for travel between the bones.

At step 806, the unified tool path is dynamically updated in response to movement of the first bone relative to the second bone without interrupting automated executing of the unified cutting stage. Cutting can be initiated by controlling a robotic device (e.g., robotic device 500) to automatically move a cutting tool (e.g., saw, reamer, burr) along the unified tool path. During execution of the unified cutting stage, the first bone may move relative to the second bone (due to movement of the first bone and/or the second bone). In response to detecting such movement (e.g., via tracking as in step 802), step 806 can dynamically update the unified tool path to account for a corresponding change in the space between the first bone and the second bone, the relative orientations of the first bone and the second bone, and/or other spatial change which reflects the relative poses of the regions of the first bone and the second bone to be resected by the cutting tool following the unified tool path. For example, the unified tool path may be compressed responsive to movement of the first bone toward the second bone, stretched responsive to movement of the first bone away from the second bone, twisted responsive to rotation of the first bone relative to the second bone, etc.

In some embodiments, step 806 includes dynamically re-planning a remainder of a cutting path for the unified cutting stage responsive to intraoperative movement of the first bone relative to the second bone, for example to re-optimize a path which may have been rendered sub-optimal by said bone movement. For example, re-planning of a remaining cutting path can be executed in response to relative poses of the first bone and the second bone changing by more than a threshold amount (e.g., greater than a threshold translation, greater than a threshold rotation). In some embodiments, dynamically updating (adjusting, replanning, etc.) the unified tool path in response to bone movement is executed without interrupting automated execution of the unified cutting stage, i.e., simultaneous with continued control of the surgical cutting tool to traverse the unified tool path. Process 800 can thereby provided for unified, automated cutting of a first bone and a second bone in accordance with a surgical plan while compensating for relative movement of the first bone and the second bone during said automated cutting.

Figure 9:
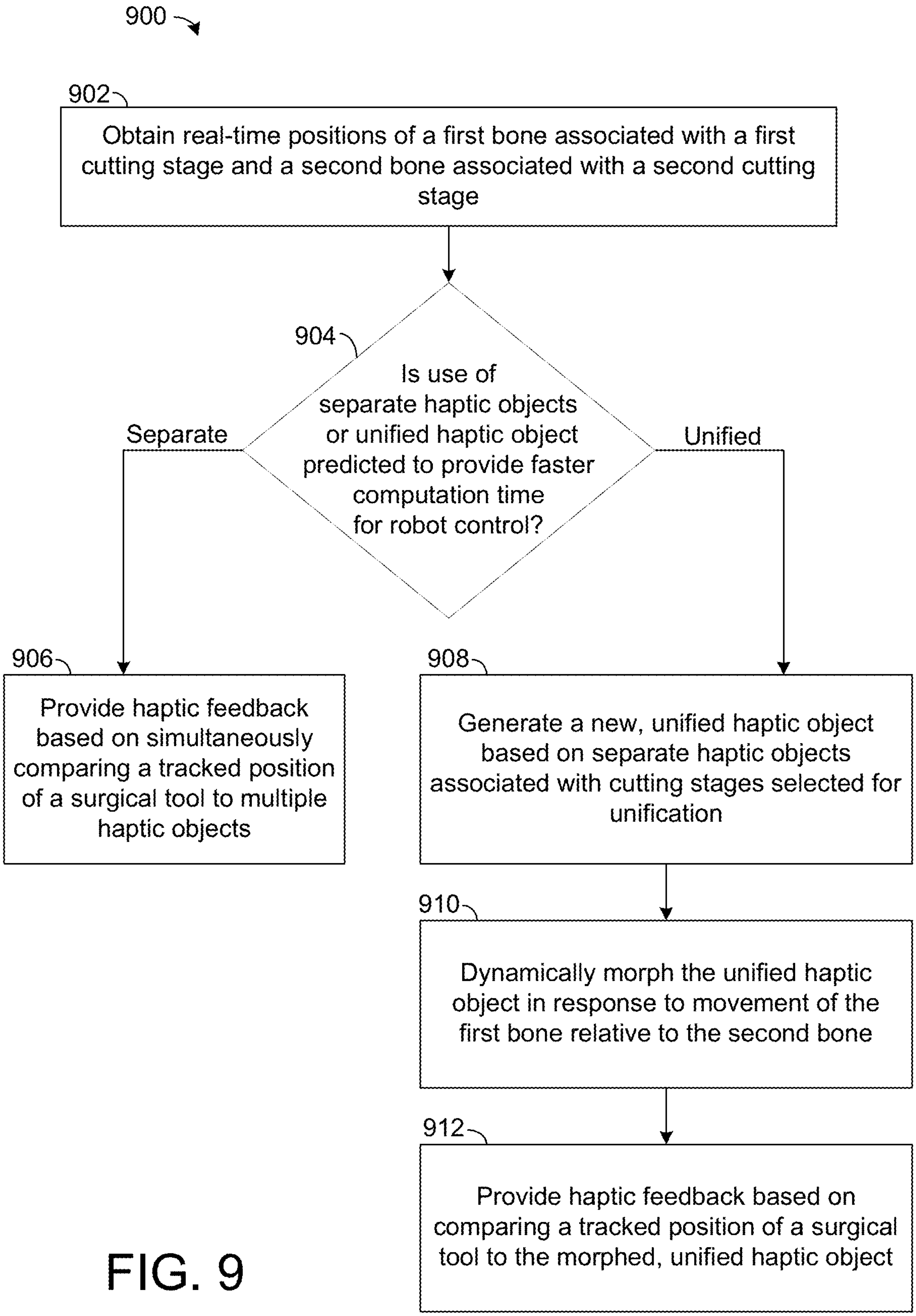
FIG. 9 is a flowchart of a process of controlling a surgical robot, according to some embodiments.

Referring now to FIG. 9, a flowchart of a process 900 for providing haptic feedback is shown, according to some embodiments. Process 900 can be executed as part of steps 716 and 718 of process 700, for example as part of step 612 of process 600. Process 900 can be executed by surgical system 200, for example by computing system 224 and/or combination of computing components, robot controllers, processors, etc. as may be included in various robotically-assisted surgical systems. Process 900 can be executed to control robotic device 500 of FIG. 5, for example. Process 900 can be executed as implemented as part of and/or using process 300 and/or process 400, for example in the bone preparation workflow of step 410 of process 400.

At step 902, real-time positions of a first bone and a second bone are obtained. A surgical plan include a first cutting stage for modifying the first bone and a second cutting stage for modifying the second bone, with the first cutting stage and the second cutting stage selected for unification and automated execution, for example via process 600 and/or process 700. The real-time positions of the first bone and the second bone can be obtained by optically tracking at least one first marker coupled to the first bone and at least one second marker coupled to the second bone (e.g., fiducial trees 240 and 241 as in FIG. 2), for example using an optical tracking system 222 as in FIG. 2, and/or otherwise tracked using another tracking modality (e.g., mechanical tracking, electromagnetic tracking, image processing, etc.). Step 902 can include dynamically updating relative positions of virtual models of the first bone and the second bone in a virtual modeling coordinate system based on tracked relative movement of the first bone and the second bone.

At step 904, a determination is made as to whether separate haptic objects or a unified haptic object is predicted to provide faster computation time for robot control. During operational control of the robotic device 500 and/or other robot as contemplated herein, control circuitry (e.g., computer, controller, etc.) computes force feedback to be generated by the robot based on position of one or more haptic interaction points defined relative to surgical end effector of the robotic device 500 (e.g., one or more points on saw blade 516, one or more points on other surgical tools) relative to one or more haptic boundaries. Faster computation speeds in such control can provide higher responsiveness to movement of the end effector, control which feels immediate, continuous, etc. to the user, while slower computation speeds can cause a lag between end effector movement and force feedback computation and control outputs. Advantageously, step 904 predicts which of multiple approaches for providing unified haptic control in step 904 will provide faster computation time for online robot control.

As shown in FIG. 9, in step 904 both use of separate haptic object and use of a unified haptic object are assessed. When separate haptic objects for the first cutting stage and the second cutting stage are used for online robot control, the control system may repeatedly calculate distances between a haptic interaction point on the surgical tool of the robotic device and determine multiple forces accordingly while combining or otherwise handling different force feedback associated with the different haptic objects. When a unified haptic object is used for online robot control (e.g., generated as in step 908 below), the control system may only need to calculate distances between the haptic interaction point and the one, unified haptic object, thereby potentially saving computational time during online control as compared to a scenario where separate haptic objects are used. However, in some scenarios, the separate haptic objects may have simpler geometric shapes and/or otherwise be represented more simply than the unified haptic object in a three-dimensional modeling space (in some embodiments, by virtue of being predefined shapes associated with implants for installation in a procedure), while the unified haptic object may have a more complex geometry resulting from unification of geometries associated with the first and second cutting stages, which may increase the computational complexity of use of the unified haptic object by more than the savings achieved by using a lower number of haptic objects. Accordingly, depending on different geometries associated with a surgical plan, including relative poses and space between regions to be resected in a first cutting stage and a second cutting stage, it may be more or less computationally efficient for online robot control to use separate haptic objects or a unified haptic object.

Step 904 can accordingly include predicting (estimating, forecasting, etc.) computation times associated with the separate haptic objects approach and the unified haptic object approach and/or assessing a proxy for such computation times. Such prediction can be based on density of surface meshes used to represent the various haptic objects which would be in use (e.g., where flatter or otherwise more-regular geometries can be represented by lower-density meshes while complex, irregular geometries require more points in a surface meshes to represent such irregularities) and which influences computational complexity. Such prediction can also be based on a degree of overlap or similarity between the separate haptic objects, i.e., an assessment as to whether substantially redundant calculations would be provided for calculations associated with separate haptic objects that substantially align in certain regions. Various simulation techniques can be used in step 904 to determine computational times or other variable(s) representative of computational complexity, computational load, etc. associated with the different approaches. Step 904 can thereby culminate in a determination as to the computationally faster, for online robot control, between different approaches for providing haptic control which unifies the first cutting stage and the second cutting stage.

If use of separate haptic objects is determined to be more computationally efficient in step 904, process 900 proceeds to step 906 where haptic feedback is provided based on simultaneously comparing a tracked position of a surgical tool to the multiple, separate haptic objects. For example, step 906 can include comparing a position of a surgical tool, robotic end effector, etc. to a first haptic object associated with the first cutting stage and a second haptic object associated with the second cutting stage (and, in some embodiments, to one or more additional haptic objects associated with unifying the cutting stages, providing a path between the haptic objects, etc.). Step 906 can include automatically determining, during online control, points at which a first haptic object overrides the second haptic object, portions of the first haptic object or second haptic object to be deactivated to allow movement between the haptic objects, determining combined force feedback to be provided based on interactions with both the first haptic object and the second haptic object, and/or other computations for determining force feedback in a manner which enables unified execution of the unified cutting stage. Where the first haptic object is associated with a first bone and the second haptic object is associated with a second bone, step 906 can include automatically moving the first haptic object relative to the second haptic object in response to tracked movement of the first bone relative to the second bone. The unified cutting stage can thus be carried out by a surgeon manipulating the surgical tool through the first and second haptic objects while the first and second haptic objects are both used online to control the robot (e.g., robotic device 500) to provide force feedback that constrains the surgical tool to the first and second haptic objects, including in scenarios where the haptic objects are associated with different bones that move relative to one another during execution of the unified cutting stage.

If use of a unified haptic object is determined to be more computationally efficient in step 904, process 900 proceeds to step 908 where a new, unified haptic object is generated based on the separate haptic objects. Step 908 can provide a unified (e.g., continuous) virtual geometry (surface, etc.) which bounds positions to be reached by a surgical tool during performance of the unified cutting stage (e.g., based on a combination of positions to be reached in first and second stages selected for unification). Step 908 can include melding a first haptic object associated with a first cutting stage together with a second haptic object associated with the second cutting stage, for example by stitching together the haptic objects along lines of intersection and then removing any segments which are thereby rendered internal to the unified haptic object. Step 908 can include generating a surface mesh (e.g., polygonal mesh) which defines the unified haptic object based on geometries associated with the first cutting stage and the second cutting stage. Various computer modeling approaches, computer-aided-design techniques, model visualization techniques, etc. can be executed in step 908 to provide the unified haptic object.

In step 910, in a scenario where the unified haptic object spans two bones to be modified in the unified cutting stage, the unified haptic object is morphed in response to movement of the first bone relative to the second bone. Morphing the unified haptic object can including stretching, compressing, twisting, etc. a region of the unified haptic object which extends across a space between the first and second bones (e.g., which provides a path between the first and second bones) to account for relative movement of the first and second bones. Morphing the unified haptic object can be performed without interrupting operation of the surgical tool, in some embodiments. Morphing the unified haptic object can be performed subject to a constraint on density of a surface mesh representing the unified haptic object, for example such that the points on the surface mesh are repositioned to morph the unified haptic object until such a constraint is reached, at which point at least a portion of the unified haptic object is re-meshed based on updated relative positions of the first and second bone. Various such techniques can be implemented to provide for dynamic morphing of the unified haptic object based on bone movement during online control without compromising computational efficiency for force feedback generation as determined in step 904.

At step 912, haptic feedback is provided by controlling a robot (e.g., robotic device 500) based on comparing a tracked position of a surgical tool (e.g., saw blade 516, other surgical end effector of the robotic device 500) to the morphed, unified haptic object. The surgical tool can be moved by a surgeon to complete the unified cutting stage while force feedback is applied by the robot based on the unified haptic object (e.g., to constrain the surgical tool to unified haptic object). A unified, haptic cutting stage is thereby provided in step 912. Advantageously, process 900 can thereby provide a unified haptic cutting stage using different techniques for providing haptic feedback associated with geometries associated with different cutting stages based on which technique may be best suited for online use in robot control for a particular surgical plan, particular patient, particular cutting operation, etc., according to various embodiments.

Figure 10:
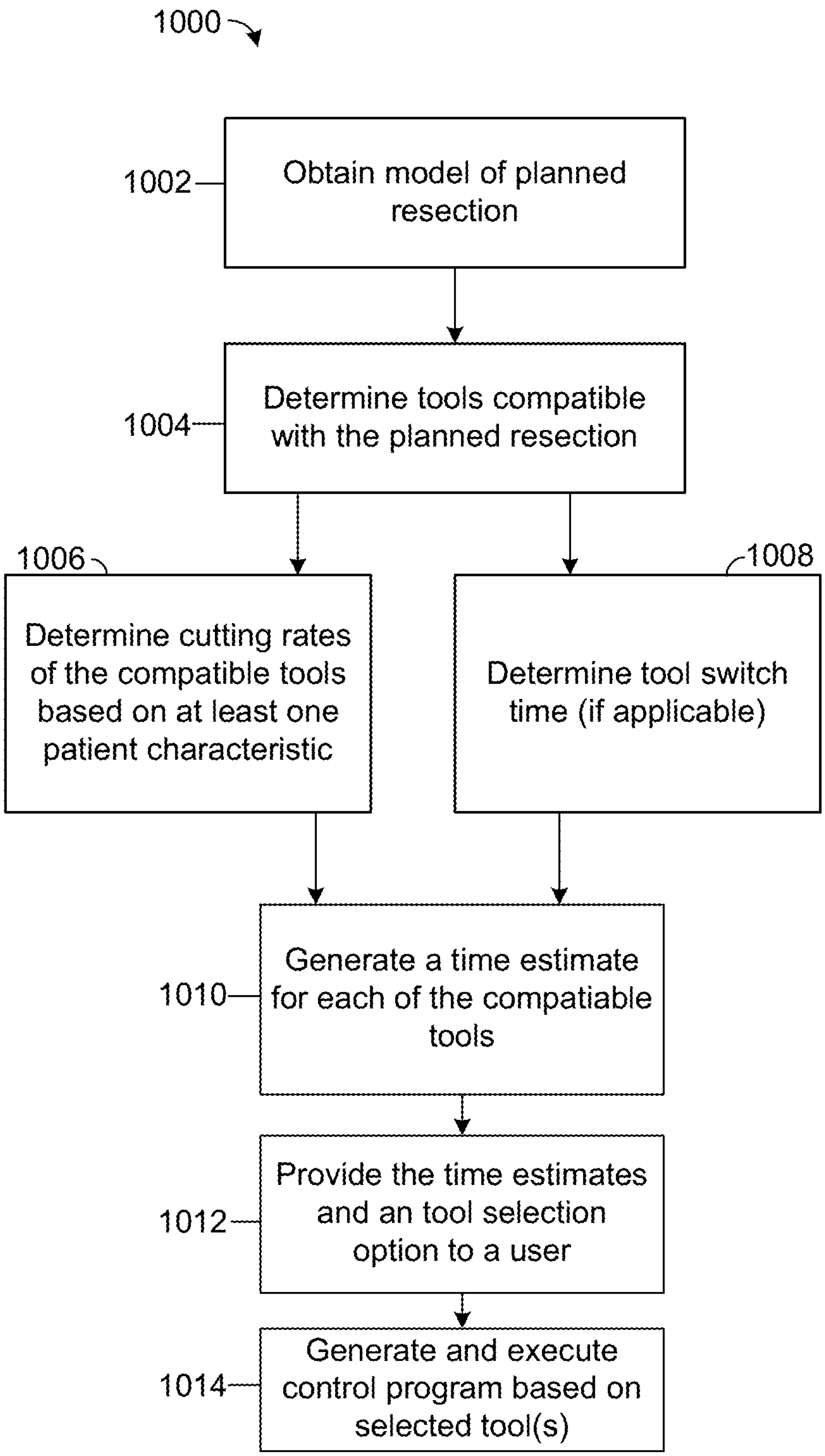
FIG. 10 is a flowchart of a process relating to control of a surgical robot, according to some embodiments.

Referring now to FIG. 10, a flowchart of a process 1000 for providing control of a selected tool including providing time estimates for compatible tools is shown, according to some embodiments. Process 1000 can be executed in combination with the various other processes herein, for example providing time estimates to user interfaces presented in at least steps 706, 714, 608, and/or 614 of FIGS. 6-7 above. Process 1000 can be executed by surgical system 200, for example by computing system 224 and/or combination of computing components, robot controllers, processors, etc. as may be included in various robotically-assisted surgical systems. Process 1000 can be executed to control robotic device 500 of FIG. 5, for example. Process 1000 can be executed as implemented as part of and/or using process 300 and/or process 400, for example in the planning workflow of step 408 and the bone preparation workflow of step 410 of process 400.

At step 1002, a model of a planned resection is obtained. The model of the planned resection can be obtained based one or more planned implant positions, for example as described with reference to the implant planning workflow of step 408 of FIG. 4 and/or steps 302-304 of FIG. 3. The model of the planned resection can be a three-dimensional representation of bone planned for removal from a bone of the patient, for example defined relative to and based on a bone model of the patient's bone (e.g., derived from CT imaging or other medical imaging).

At step 1004, tools compatible with the planned resection are determined. The tools can be determined from a set of available tools, for example including saws, reamers, burrs, drill bits, etc. of different sizes, shapes, etc. In some embodiments, the set of available tools may all be useable with the robotic device 500, e.g., as different end effectors attached to the robotic device 500. Step 1004 can include determine which of the tools are compatible with the planned resection, for example based on a shape and/or size of the planned resection. For example, a cutting tool with a cutting end which is larger than at least a portion of the planned resection (e.g., a saw with a cutting end wider than a region to be resected without resecting neighboring regions) may be determined to be incompatible with the planned resection. As another example, a cutting tool with an overall geometry which prevents it from reaching certain areas of the planned resection (e.g., a reamer having too short of a shaft to reach the full extent of a planned resection) may be deemed incompatible with the planned resection. Accordingly, step 1004 can include eliminating incompatible tool options and identifying compatible tool options to generate a list of one or more tools compatible with the planned resection. In some embodiments, step 1004 can include determining that a set of tools is compatible with the planned resection as a group, i.e., that the planned resection can be completed by using a first tool to complete a first portion of the planned resection and second tool to complete a second portion of the planned resection.

At step 1006, cutting rates of the eligible tools is determined based on at least one patient characteristic. Cutting rates of the eligible tools indicate, for each eligible tool, a rate at which that tool can execute the bone resection, for example in units of cut volume or distance per unit time (e.g., $mm^3/s$, mm/s, etc.). In some embodiments, the patient characteristic is bone density, for example an average bone density of bone to be cut to provide the planned resection and/or multiple bone density values associated with different portions of the planned resection. Step 1006 can include determining said bone density value(s) from pre-operative imaging data (e.g., CT data) for the bone or bones on which the planned resection is to be performed, for example based on data associated with a bone model where the bone model intersects with the model of the planned resection obtained in step 1002. Step 1006 can include determining cutting rates for eligible tools as functions of such bone density and tool characteristics (e.g., size, power, type, etc.); for example, certain types of tools may be more affected by variation in bone density than others (e.g., higher density may slow cutting rate for a first cutting tool by a first amount and for a second cutting tool by a second cutting amount relative to cutting rates at a lower density). Other patient characteristics may be used to determine cutting rates as additional or alternative variables in such functions, for example bone type (e.g., cortical, cancellous, trabecular), resection geometry (e.g., smooth or flat surface may have higher cutting rate than irregular surfaces), body mass index or other characteristics relating to surgical access (e.g., fatty tissue of certain patients may restrict access by certain tools and thus reduce cutting rates, potentially different for different types of tools having different geometries), bone defects (e.g., certain bone defects, conditions, diseases, etc.), and/or various other patient characteristics in various embodiments. In some embodiments, functions are pre-programmed and stored for each possible cutting tool which can be called in step 1006 and applied to the at least one patient characteristic(s) to calculate cutting rates for the eligible tools.

At step 1008, a tool switch time is determined for applicable scenarios. In particular, if step 1004 determines that the planned resection could be completed by using a first tool followed by a second tool, step 1008 is executed to predicted an amount of time (duration) for switching between the first tool and the second tool during execution of the planned resection. In some embodiments, switching from a first tool to a second tool can include detaching the first tool from a robotic arm (e.g., removing the sagittal saw blade 516 from the housing 512, removing surgical device 506 from robotic arm 504) and attaching the second tool to the robotic arm (e.g., coupling a different sized saw blade to the housing 512, coupling a different surgical device to the robotic arm, introducing a passive joint between the robotic arm and the surgical device 506 or a different surgical device, verifying proper attachment via a verification step using a probe or other approach, etc.). In some embodiments, step 1008 can determine the amount of time for such a tool switch by retrieving a time estimate from a look-up table based on the tools to be switched between (e.g., based on types of the first tool and the second tool) (e.g., a table pre-populated by a manufacturer based on experimental data) or by applying the set of tools to be used as inputs to a machine learning model trained on measured tool switching times from prior operations or experiments. A duration of time expected to be used in switching between tools can thereby be determined in step 1008 for one or more tool combinations compatible with the planned resection.

At step 1010, a time estimate (estimated durations) for completing the planned resection is generated for each of the eligible tools (or combination of tools). The time estimates can be generated in step 1010 based on the cutting rates from step 1006, the tool switch times from 1008 (where applicable), and, in some embodiments, the model of the planned resection from step 1002. For example, step 1010 can include determining a size of the resection based on the model of the planned resection, for example an amount of bone volume to be cut to complete the planned resection and/or a distance to be traversed by an eligible tool to complete the planned resection. Step 1010 can include calculating products of the determined size of the resection and the cutting rates for the relevant tools. In some embodiments, step 1010 is based on different paths, positions, etc. which would need to be followed by different tool types (e.g., one type of tool may resect an outer boundary of a planned resection, while another type of tool may obliterate an entire bone volume within the planned resection, such that the positions needed to be reached to complete the planned resection are different; such differences can be considered in step 1010). Where a time estimate for use of a combination of tools is determined in step 1010, step 1010 can include calculating a first product of a first cutting rate for a first tool with a size of a first portion of the resection to be completed with the first tool and a second product of a second cutting rate for a second tool with a size of a second portion of the resection to be completed with the second tool, and summing the first product and the second product together with a tool switch time for switching between the first tool and the second tool as determined in step 1008. Step 1010 can include repeating such calculations as may be suitable for any number of tools and/or tool combinations deemed compatible with completing the planned resection in step 1004.

In step 1012, the time estimates and a tool selection option are provided to a user, for example via a graphical user interface (e.g., via display 264 as in FIG. 2 and/or a graphical user interface presented on a personal computing device (e.g., laptop or desktop computer, etc.)). The graphical user interface can provide a list of the tools and/or tool combinations deemed compatible with the planned resection in step 1004, together with time estimates for such options as generated in step 1010. The graphical user interface can thus allow a user to compare the time estimates for the different tool options compatible with a planned resection, and to select a prefer tool or combination of tools for use in executing the planned resection. In some embodiments, step 1012 includes automatically sorting the list of tools and/or tool combinations based on the generated time estimates (e.g., such that the tools corresponding to shorter estimated times for resection completion are presented first, higher on the list, etc.). In some embodiments, a tool or combination of tools having the shortest time estimate of all compatible tools (i.e., of all time estimates generated in step 1010) is automatically selected, selected as a default, etc. (e.g., for user approval, such that a user must opt-out to select a different tool, etc.). Accordingly, tool selection for executing the planned resection can proceed based on the tool eligibility and time estimates generated in steps 1004-1010.

At step 1014, a control program is generated and executed based on the tool or combination of tools selected in step 1012. Step 1014 can included path planning to generate a path for automated resection based on the selected tool(s) and/or generating one or more haptic objects for constraining the selected tool(s) for providing haptic feedback during executing of the planned resection. Step 1014 can be executed based on characteristics of the selected tool(s), for example because a larger tool may need to pass through fewer positions of an autonomous path to resect the same bone as a smaller tool or because a larger tool may need to be constrained to fewer positions to be constrained to a planned resection as compared to a smaller tool. Geometric relationships between cutting tips of different tools and a robotic device (e.g., robotic arm) on which such tools are mounted will also differ across tools, such that step 1014 can generate control programs which are adapted to the geometry associated with selected tool(s). Step 1014 can then include executing such control programs such that a robot (robotic device, robotic arm, etc. as described herein) is controlled to automatically execute and/or guide completion of the planned resection using the selected tool or combination of tools.

The planned resection can thereby be executed in accordance with user selections and preferences and based on the time estimates generated in process 1000. Process 1000 can be executed as part of the various other processes, teachings, systems, robots, etc. described herein, for example combined with user selection between automated and haptic control approaches, so as to provide user customizability of the tools used and the control modality used for completing a planned resection and carrying out a surgical plan as may be suitable for different surgeon preferences, different patients, different clinical scenarios, and the like.

Configuration of Exemplary Embodiments

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, magnetic, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations, for example non-transitory computer-readable media. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

Examples of the present disclosure include a first example including a robotically-assisted surgical system which includes a robot and a computer system. The computing system is programmed to determine whether a first cutting stage of a surgical plan is compatible with a second cutting stage of the surgical plan by comparing first characteristics of the first cutting stage with second characteristics of the second cutting stage and control the robot to provide, responsive to a determination that the first cutting stage is incompatible with the second cutting stage, the first cutting stage and the second cutting stage sequentially and provide, responsive to a determination that the first cutting stage is compatible with the second cutting stage, a unified cutting stage based on the first cutting stage and the second cutting stage.

In some implementations of that example, the computer system is programmed to provide the unified cutting stage by generating a unified virtual geometry based on a first virtual geometry associated with the first cutting stage and a second virtual geometry associate with the second cutting stage. The computer system may be further programmed to determine, responsive to the determination that the first cutting stage is compatible with the second cutting stage, whether the unified cutting stage is automatable. The computing system may be further programmed to generate a first control program responsive to the unified cutting stage being automatable and generate a second control program responsive to the unified cutting stage not being automatable.

A second example of the present disclosure is at least one non-transitory computer-readable medium storing program instructions that, when executed by at least one processor, causes the at least one processor to perform operations including determining a plurality of tools compatible with a planned resection, generating time estimates for completing the planned resection based on cutting rates of the plurality of tools and a patient characteristic, causing display of the time estimates to a user together with options for selecting between the plurality of tools, and generating and executing a control program for executing the planned resection based on a user selection of one or more of the plurality of tools. In some embodiments, generating the time estimates is further based on a tool switch time associated with switching between use of a first tool and use of a first tool during execution of the planned resection.

What is claimed is:

1. A robotically-assisted surgical system for orthopedic surgery, comprising:
- a robot; and
- a computer system programmed to:
  - provide, via a graphical user interface, a user with an option to combine a first cutting stage of a surgical plan with a second cutting stage of the surgical plan, wherein the first cutting stage and the second cutting stage comprise sculpting different regions of bone, and wherein the computing system is programmed to provide the option in response to the computing system determining that the first cutting stage is eligible for combination with the second cutting stage by comparing first characteristics of the first cutting stage with second characteristics of the second cutting stage;
  - abstain from providing the user with the option to combine the first cutting stage with the second cutting stage in response to the computing system determining that the first cutting stage is ineligible for combination with the second cutting stage by comparing the first characteristics with the second characteristics; and
  - control the robot to:
    - provide, absent selection of the option, the first cutting stage and the second cutting stage sequentially; and
    - provide, in response to user selection of the option, a unified cutting stage based on the first cutting stage and the second cutting stage.

2. The robotically-assisted surgical system of claim 1, wherein the computer system is programmed to provide the unified cutting stage by planning a unified tool path which intersects both a first resection region associated with the first cutting stage and a second resection region associated with the second cutting stage.

3. The robotically-assisted surgical system of claim 1, wherein the computer system is programmed to provide the unified cutting stage by generating a unified haptic boundary based on a first haptic boundary associated with the first cutting stage and a second haptic boundary associated with the second cutting stage.

4. The robotically-assisted surgical system of claim 1, wherein:
- the first cutting stage comprises a first resection of a first bone;
- the second cutting stage comprises a second resection of a second bone;
- the robotically-assisted surgical system comprises a tracking system configured to track relative positions of the first bone and the second bone; and
- the computer system is programmed to provide the unified cutting stage by dynamically adjusting a control path or boundary for the unified cutting stage based on changes in the relative positions of the first bone and the second bone.

5. The robotically-assisted surgical system of claim 1, wherein the computer system is further programmed to:
- predict a first duration of providing the first cutting stage and the second cutting stage sequentially;
- predict a second duration of providing the unified cutting stage; and
- cause a graphical user interface to display the first duration, the second duration, and the option to the user.

6. The robotically-assisted surgical system of claim 5, wherein the computer system is programmed to predict the first duration and the second duration based on density of bone planned for resection in the first cutting stage and the second cutting stage.

7. The robotically-assisted surgical system of claim 5, wherein the computer system is programmed to predict the first duration by determining a first tool eligible for use in executing the first cutting stage, a second tool eligible for use in executing the second cutting stage, and an amount of time for switching between the first tool and the second tool.

8. The robotically-assisted surgical system of claim 1, further comprising determining whether the unified cutting stage is eligible for automated execution based on the first characteristics and the second characteristics.

9. The robotically-assisted surgical system of claim 8, wherein the computer system is programmed to control the robot to provide the automated execution in response to a combination of the user selection of the option, a determination that the unified cutting stage is eligible for the automated execution, and a user input requesting initiation of the automated execution.

10. The robotically-assisted surgical system of claim 1, further comprising tools configured for use with the robot, wherein the computer system is further programmed to:

identify a subset of the tools eligible for performance of the unified cutting stage; and provide a list of the subset of the tools to the user with the option.

11. The robotically-assisted surgical system of claim 1, wherein the computer system is programmed to provide the unified cutting stage by:

predicting a computational load associated with controlling the robot simultaneously using both a first haptic object associated with the first cutting stage and a second haptic object associated with the second cutting stage;

if the computational load is predicted to exceed a computational limit associated with robot control, generating a unified haptic object based on the first haptic object and the second haptic object and providing the unified cutting stage by controlling the robot using the unified haptic object; and if the computational load is predicted to not exceed the computational limit, providing the unified cutting stage by controlling the robot simultaneously using both the first haptic object and the second haptic object.

12. A method for robotically-assisted surgery for orthopedic surgery comprising a robot and a computing system, wherein the computing system performs the method by:

generating, and providing to a user via an graphical user interface, an option to combine a first cutting stage of a surgical plan with a second cutting stage of the surgical plan, wherein the first cutting stage and the second cutting stage comprise sculpting different regions of bone, and wherein the method comprises providing the option in response to the computing system determining that the first cutting stage is eligible for combination with the second cutting stage by comparing first characteristics of the first cutting stage with second characteristics of the second cutting stage;

abstaining from providing the user with the option to combine the first cutting stage with the second cutting stage in response to the computing system determining that the first cutting stage is ineligible for combination with the second cutting stage by comparing the first characteristics with the second characteristics; and controlling the robot by:

generating, in response to the rejection absent selection of the option, a first control boundary or path for the first cutting stage and a second control boundary or path for the second cutting stage, the first control boundary or path distinct from the second control boundary or path so as provide the first cutting stage and the second cutting stage sequentially; and generating, in response to the selection of the option, a unified control boundary or path for unified execution of the first cutting stage and the second cutting stage as a unified cutting stage.

* * * * *